(12) United States Patent
Yoshida et al.

(10) Patent No.: US 7,319,129 B2
(45) Date of Patent: Jan. 15, 2008

(54) SILSESQUIOXANE DERIVATIVE AND PROCESS FOR PRODUCING THE SAME

(75) Inventors: Kazuhiro Yoshida, Kanagawa (JP); Yoshitaka Morimoto, Kanagawa (JP); Kenichi Watanabe, Kanagawa (JP); Nobumasa Ootake, Kanagawa (JP)

(73) Assignee: Chisso Corporation, Osaka (JP)

( * ) Notice: Subject to any disclaimer, the term of this patent is extended or adjusted under 35 U.S.C. 154(b) by 274 days.

(21) Appl. No.: 10/527,751

(22) PCT Filed: Sep. 3, 2003

(86) PCT No.: PCT/JP03/11277

§ 371 (c)(1),
(2), (4) Date: Oct. 19, 2005

(87) PCT Pub. No.: WO2004/024741

PCT Pub. Date: Mar. 25, 2004

(65) Prior Publication Data

US 2006/0052623 A1    Mar. 9, 2006

(30) Foreign Application Priority Data

Sep. 13, 2002    (JP) .............................. 2002-268717

(51) Int. Cl.
   C08G 77/04    (2006.01)
(52) U.S. Cl. .......................................... 528/34; 528/43
(58) Field of Classification Search .................... None
   See application file for complete search history.

(56) References Cited

U.S. PATENT DOCUMENTS

| 6,927,270 B2 * | 8/2005 | Lichtenhan et al. ........... 528/12 |
| 2003/0018109 A1 * | 1/2003 | Hsiao et al. ................. 524/269 |
| 2004/0249103 A1 | 12/2004 | Morimoto et al. | |

FOREIGN PATENT DOCUMENTS

WO    03/024870    3/2003

OTHER PUBLICATIONS

Knight, Christopher. "A two-dimensional silicon-29 nuclear magnetic resonance spectroscopic study of the structure of the silicate anions present in an aqueous potassium silicate solution", Journal of the Chemical Society, Dalton Transactions, No. 6, 1988, pp. 1457-1460.

Loy, Douglas A. et al., "Bridged Polysilsesquioxanes. Highly Porous Hybrid Organic-Inorganic Materials", Chem. Rev. 95, 1995, pp. 1431-1442.

Feher, Frank J. et al., "Facile Syntheses of New Incompletely Condensed Polyhedral Oligosilsesquioxanes", Organometallics, 10, 1991, pp. 2526-2528.

Shchegolikhina, Olga et al., "Synthesis and Structure of Sodium Phenylsiloxanolate", Organometallics, 19, 2000, pp. 1077-1082.

Poss Chemical Catalog, Hybrid Plastics, Feb. 2001.

* cited by examiner

Primary Examiner—Marc S. Zimmer
(74) Attorney, Agent, or Firm—Wenderoth, Lind & Ponack, L.L.P.

(57) ABSTRACT

The silsesquioxane derivative of the invention is represented by Formula (1), and it may be utilized as additives to ordinary organic polymers for improving the flame retardancy, heat resistance, weather resistance, light resistance, electric insulating property, surface property, hardness, mechanical strength and chemical resistance thereof.

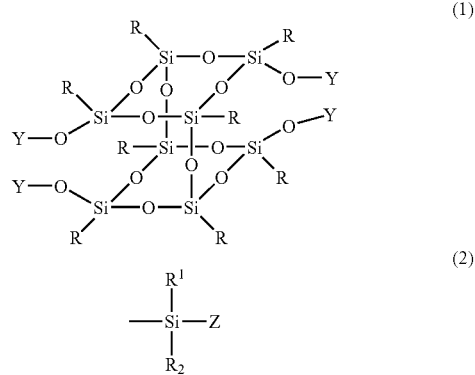

In Formula (1), R is hydrogen, alkyl, aryl or arylalkyl; at least one Y is a group represented by Formula (2) and the other Y is hydrogen; in Formula (2), $R^1$ and $R^2$ are a group independently defined similarly to R; and Z is preferably a functional group, or a group having a functional group.

26 Claims, No Drawings

SILSESQUIOXANE DERIVATIVE AND PROCESS FOR PRODUCING THE SAME

TECHNICAL FIELD

The present invention relates to a silsesquioxane derivative and to a method for producing it. The silsesquioxane derivative can be used for electronic materials, optical materials, electro-optical materials or catalyst carriers, and can also be utilized for additives for improving the properties of general organic polymers. Examples of the properties are flame retardancy, heat resistance, weather resistance, light resistance, electric insulating property, surface property, hardness, mechanical strength and chemical resistance.

In the invention, silsesquioxane is used as a generic term of a compound obtained through hydrolysis and condensation of a trifunctional hydrolyzable silicon compound. In the following description, silsesquioxane may be represented by an abbreviation, PSQ.

BACKGROUND ART

A lot of studies have heretofore been made, relating to PSQ. Baney et al's general review shows a ladder structure, a completely-condensed structure, an incompletely-condensed structure and an amorphous structure, as the structure of PSQ of which the existence has been confirmed (Reference 1). The completely-condensed structure is a structure in which plural cyclic structures form closed spaces and the shape of the closed spaces is not defined. The incompletely-condensed structure differs from the completely-condensed structure in that at least one site of the latter is not closed and the space thereof is not closed.

Feher, et al. obtained an incompletely-condensed structure PSQ by hydrolyzing cyclopentyltrichlorosilane or cyclohexyltrichlorosilane in acetone (Reference 2). Shchegolikhinea, et al. obtained a cyclic tetramer PSQ having a terminal of Si—O—Na, by hydrolyzing phenyltributoxysilane with an equimolar amount of sodium hydroxide and an equimolar amount of water in butanol (Reference 3).

However, there has been reported no example of synthesizing PSQ having a completely-condensed or incompletely-condensed structure according to the Shchegolikhinea et al's method. Of PSQ having a completely-condensed or incompletely-condensed structure, there are not so many types of compounds that have been easily synthesized and isolated. Of those, the number of commercially-available ones is further limited. Recently, PSQ derivatives produced by introducing various functional groups into PSQ having a completely-condensed or incompletely-condensed structure have been put on the market by Hybrid Plastics, and various applications have been proposed from them (Reference 4).

Reference 1: Chem. Rev. 95, 1409 (1995),
Reference 2: Organometallics, 10, 2526 (1991),
Reference 3: Organometallics, 19, 1077 (2000),
Reference 4: POSS CHEMICAL CATALOG, Hybrid Plastics (February 2001).

However, there are known only a few types of basic backbones of commercially-available PSQ derivatives, including organosilicon groups except a bonding state represented by $SiO_{3/2}$. Accordingly, in order to effectively utilize PSQ derivatives having a completely-condensed structure or an incompletely-condensed structure in broad applications, it is desired to provide a PSQ derivative having a novel backbone structure. It is also important that the derivative can be produced within a shorter period of time at lower costs than conventional ones. Further, already-existing PSQ derivatives have another problem in that they are not compatible with general organic polymers. They could not be uniformly mixed with polymers; and when they are in coating films, they may whiten the films or they may bleed out of the films. Accordingly, their amount to be added is limited. For these reasons, some PSQ could not satisfactorily impart the characteristics expected of PSQ to polymers. Therefore, in order to broaden the applicability of PSQ, the compatibility thereof with general organic polymers must be improved. To solve the problems with the conventional PSQ derivatives, the present invention provides a novel PSQ derivative and a method for producing it within a short period of time at low costs.

DISCLOSURE OF THE INVENTION

The above-mentioned problems can be solved by the invention that comprises the following constitution.

[1] A silsesquioxane derivative represented by Formula (1):

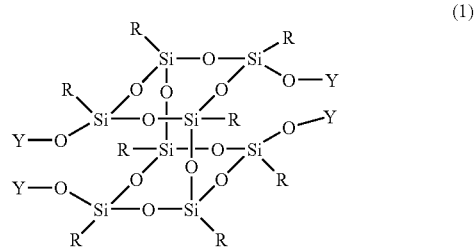

(1)

wherein each R is a group independently selected from hydrogen, alkyl having 1 to 45 carbon atoms in which any hydrogen may be replaced by fluorine and any —$CH_2$— may be replaced by —O—, —CH=CH—, cycloalkylene or cycloalkenylene, substituted or unsubstituted aryl, and arylalkyl composed of a substituted or unsubstituted aryl group and an alkylene group in which any hydrogen may be replaced by fluorine and any —$CH_2$— may be replaced by —O—, —CH=CH— or cycloalkylene; at least one Y is a group selected from the group represented by Formula (2), and the other Y is hydrogen; when at least two Y's are a group represented by Formula (2), then they may be the same group or may be composed of at least two different groups;

(2)

wherein $R^1$ and $R^2$ are independently a group defined similarly to R; and Z is a group defined similarly to R, or a functional group, or a group having a functional group.

[2] The silsesquioxane derivative described in item [1], wherein each R is a group independently selected from hydrogen, alkyl having 1 to 45 carbon atoms in which any hydrogen may be replaced by fluorine and any —$CH_2$— may be replaced by —O—, —CH=CH—, cycloalkylene or cycloalkenylene, substituted or unsubstituted aryl, and arylalkyl composed of a substituted or unsubstituted aryl group and an alkylene group in which any hydrogen may be replaced by fluorine and any —CH$_2$— may be replaced by —O—, —CH=CH— or cycloalkylene; $R^1$ and $R^2$ are independently methyl, isopropyl, tert-butyl or phenyl; and Z is a group defined similarly to R, or a functional group, or a group having a functional group.

[3] The silsesquioxane derivative described in item [2], wherein each R is a group independently selected from hydrogen, and alkyl having 1 to 30 carbon atoms in which any hydrogen may be replaced by fluorine and any —CH$_2$— may be replaced by —O— or cycloalkylene.

[4] The silsesquioxane derivative described in item [2], wherein each R is a group independently selected from alkenyl having 2 to 20 carbon atoms in which any hydrogen may be replaced by fluorine and any —CH$_2$— may be replaced by —O— or cycloalkylene, and alkyl having 1 to 20 carbon atoms in which any hydrogen may be replaced by fluorine and at least one —CH$_2$— is replaced by cycloalkenylene.

[5] The silsesquioxane derivative described in item [2], wherein each R is a group independently selected from phenyl in which any hydrogen may be replaced by halogen or alkyl having 1 to 10 carbon atoms, and naphthyl; in the alkyl as the substituent for the phenyl, any hydrogen may be replaced by fluorine and any —CH$_2$— may be replaced by —O—, —CH=CH—, cycloalkylene or phenylene; and when the phenyl has plural substituents, the substituents may be the same group or different groups.

[6] The silsesquioxane derivative described in item [2], wherein each R is a group independently selected from phenylalkyl composed of a phenyl group in which any hydrogen may be replaced by halogen or alkyl having 1 to 10 carbon atoms and an alkylene group having 1 to 12 carbon atoms; in the alkyl as the substituent for the phenyl group, any hydrogen may be replaced by fluorine and any —CH$_2$— may be replaced by —O—, —CH=CH—, cycloalkylene or phenylene; in the alkylene group, any hydrogen may be replaced by fluorine and any —CH$_2$— may be replaced by —O— or cycloalkylene; and when the phenyl group has plural substituents, the substituents may be the same group or different groups.

[7] The silsesquioxane derivative described in item [2], wherein each R is a group independently selected from phenylalkenyl composed of a phenyl group in which any hydrogen may be replaced by halogen or alkyl having 1 to 10 carbon atoms and an alkenylene group having 2 to 12 carbon atoms; in the alkyl as the substituent for the phenyl group, any hydrogen may be replaced by fluorine and any —CH$_2$— may be replaced by —O—, —CH=CH—, cycloalkylene or phenylene; in the alkenylene group, any hydrogen may be replaced by fluorine and any —CH$_2$— may be replaced by —O— or cycloalkylene; and when the phenyl group has plural substituents, the substituents may be the same group or different groups.

[8] The silsesquioxane derivative described in item [2], wherein each R is a group independently selected from alkyl having 1 to 8 carbon atoms in which any hydrogen may be replaced by fluorine and any —CH$_2$— may be replaced by —O—, —CH=CH—, cycloalkylene or cycloalkenylene, phenyl in which any hydrogen may be replaced by halogen, methyl or methoxy, phenylalkyl composed of a phenyl group in which any hydrogen may be replaced by fluorine, alkyl having 1 to 4 carbon atoms, vinyl or methoxy, and an alkylene group having 1 to 8 carbon atoms in which any —CH$_2$— may be replaced by —O—, —CH=CH— or cycloalkylene, and naphthyl; when the phenyl group of the phenyl or the phenylalkyl has plural substituents, the substituents may be the same group or different groups.

[9] The silsesquioxane derivative described in item [2], wherein all R's are the same group selected from alkyl having 1 to 8 carbon atoms in which any hydrogen may be replaced by fluorine and any —CH$_2$— may be replaced by —O—, —CH=CH—, cycloalkylene or cycloalkenylene, phenyl in which any hydrogen may be replaced by halogen, methyl or methoxy, phenylalkyl composed of a phenyl group in which any hydrogen may be replaced by fluorine, alkyl having 1 to 4 carbon atoms, vinyl or methoxy, and an alkylene group having 1 to 8 carbon atoms in which any —CH$_2$— may be replaced by —O—, —CH=CH— or cycloalkylene, and naphthyl; when the phenyl group of the phenyl or the phenylalkyl has plural substituents, the substituents may be the same group or different groups.

[10] The silsesquioxane derivative described in item [2], wherein all R's are the same group selected from phenyl in which any hydrogen may be replaced by halogen, methyl or methoxy, phenylalkyl composed of a phenyl group in which any hydrogen may be replaced by fluorine, alkyl having 1 to 4 carbon atoms, vinyl or methoxy, and an alkylene group having 1 to 8 carbon atoms in which any —CH$_2$— may be replaced by —O—, —CH=CH— or cycloalkylene, and naphthyl; when the phenyl group of the phenyl or the phenylalkyl has plural substituents, the substituents may be the same group or different groups.

[11] The silsesquioxane derivative described in item [2], wherein all R's are phenyl.

[12] The silsesquioxane derivative described in item [1], wherein each R is a group independently selected from hydrogen, alkyl having 1 to 45 carbon atoms in which any hydrogen may be replaced by fluorine and any —CH$_2$— may be replaced by —O—, —CH=CH—, cycloalkylene or cycloalkenylene, substituted or unsubstituted aryl, and arylalkyl composed of a substituted or unsubstituted aryl group and an alkylene group in which any hydrogen may be replaced by fluorine and any —CH$_2$— may be replaced by —O—, —CH=CH— or cycloalkylene; $R^1$ and $R^2$ are independently methyl, isopropyl, tert-butyl or phenyl; and Z is a functional group selected from hydrogen (bonding to Si), halogen, —OH, fluoroalkyl, alkoxy, carboxyl, 2-oxapropanedioyl, —COO—, —OCO—, polyalkyleneoxy, oxiranyl, 3,4-epoxycyclohexyl, oxetanyl, oxetanylene, alkenyl, cycloalkenyl, —NH$_2$, —NH—, —CN, —NCO, —SH and —PH$_2$, or a group having the functional group.

[13] The silsesquioxane derivative described in item [12], wherein each R is a group independently selected from hydrogen, and alkyl having 1 to 30 carbon atoms in which any hydrogen may be replaced by fluorine and any —CH$_2$— may be replaced by —O— or cycloalkylene.

[14] The silsesquioxane derivative described in item [12], wherein each R is a group independently selected from alkenyl having 2 to 20 carbon atoms in which any hydrogen may be replaced by fluorine and any —CH$_2$— may be replaced by —O— or cycloalkylene, and alkyl having 1 to 20 carbon atoms in which any hydrogen may be replaced by fluorine and at least one —CH$_2$— is replaced by cycloalkenylene.

[15] The silsesquioxane derivative described in item [12], wherein each R is a group independently selected from phenyl in which any hydrogen may be replaced by halogen or alkyl having 1 to 10 carbon atoms, and naphthyl; in the alkyl as the substituent for the phenyl, any hydrogen may be replaced by fluorine and any —CH$_2$— may be replaced by —O—, —CH=CH—, cycloalkylene or phenylene; and when the phenyl has plural substituents, the substituents may be the same group or different groups.

[16] The silsesquioxane derivative described in item [12], wherein each R is a group independently selected from phenylalkyl composed of a phenyl group in which any hydrogen may be replaced by halogen or alkyl having 1 to 10 carbon atoms and an alkylene group having 1 to 12 carbon atoms; in the alkyl as the substituent for the phenyl group, any hydrogen may be replaced by fluorine and any —CH$_2$— may be replaced by —O—, —CH=CH—, cycloalkylene or phenylene; in the alkylene group, any hydrogen may be replaced by fluorine and any —CH$_2$— may be replaced by —O— or cycloalkylene; and when the phenyl group has plural substituents, the substituents may be the same group or different groups.

[17] The silsesquioxane derivative described in item [12], wherein each R is a group independently selected from phenylalkenyl composed of a phenyl group in which any hydrogen may be replaced by halogen or alkyl having 1 to 10 carbon atoms and an alkenylene group having 2 to 12 carbon atoms; in the alkyl as the substituent for the phenyl group, any hydrogen may be replaced by fluorine and any —CH$_2$— may be replaced by —O—, —CH=CH—, cycloalkylene or phenylene; in the alkenylene group, any hydrogen may be replaced by fluorine and any —CH$_2$— may be replaced by —O— or cycloalkylene; and when the phenyl group has plural substituents, the substituents may be the same group or different groups.

[18] The silsesquioxane derivative described in item [12], wherein each R is a group independently selected from alkyl having 1 to 8 carbon atoms in which any hydrogen may be replaced by fluorine and any —CH$_2$— may be replaced by —O—, —CH=CH—, cycloalkylene or cycloalkenylene, phenyl in which any hydrogen may be replaced by halogen, methyl or methoxy, phenylalkyl composed of a phenyl group in which any hydrogen may be replaced by fluorine, alkyl having 1 to 4 carbon atoms, vinyl or methoxy, and an alkylene group having 1 to 8 carbon atoms in which any —CH$_2$— may be replaced by —O—, —CH=CH— or cycloalkylene, and naphthyl; when the phenyl group of the phenyl or the phenylalkyl has plural substituents, the substituents may be the same group or different groups.

[19] The silsesquioxane derivative described in item [12], wherein all R's are the same group selected from alkyl having 1 to 8 carbon atoms in which any hydrogen may be replaced by fluorine and any —CH$_2$— may be replaced by —O—, —CH=CH—, cycloalkylene or cycloalkenylene, phenyl in which any hydrogen may be replaced by halogen, methyl or methoxy, phenylalkyl composed of a phenyl group in which any hydrogen may be replaced by fluorine, alkyl having 1 to 4 carbon atoms, vinyl or methoxy, and an alkylene group having 1 to 8 carbon atoms in which any —CH$_2$— may be replaced by —O—, —CH=CH— or cycloalkylene, and naphthyl; when the phenyl group of the phenyl or the phenylalkyl has plural substituents, the substituents may be the same group or different groups.

[20] The silsesquioxane derivative described in item [12], wherein all R's are the same group selected from phenyl in which any hydrogen may be replaced by halogen, methyl or methoxy, phenylalkyl composed of a phenyl group in which any hydrogen may be replaced by fluorine, alkyl having 1 to 4 carbon atoms, vinyl or methoxy, and an alkylene group having 1 to 8 carbon atoms in which any —CH$_2$— may be replaced by —O—, —CH=CH— or cycloalkylene, and naphthyl; when the phenyl group of the phenyl or the phenylalkyl has plural substituents, the substituents may be the same group or different groups.

[21] The silsesquioxane derivative described in item [12], wherein all R's are phenyl.

[22] The silsesquioxane derivative described in any one of items [1] to [21], wherein Z in Formula (2) described in item [1] is halogenated alkyl or a group having halogenated alkyl.

[23] The silsesquioxane derivative described in any one of items [1] to [21], wherein Z in Formula (2) described in item [1] is alkenyl, or a group having any one of alkenyl, —OH, carboxyl, 2-oxapropanedioyl, oxiranyl, 3,4-epoxycyclohexyl, oxetanyl, oxetanylene and —NH$_2$.

[24] A method for producing the silsesquioxane derivative described in item [1], which comprises using a silsesquioxane derivative represented by Formula ):

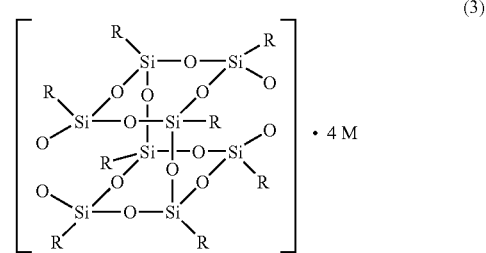

wherein R has the same meaning as that of R in Formula (1) described in item [1], and M is a monovalent alkali metal atom.

[25] A polymer obtained by using the silsesquioxane derivative described in item [23].

In the following description, the silsesquioxane derivative represented by Formula (1) may be referred to as a compound (1). The compound represented by Formula (3) may be referred to as a compound (3). The same expression shall apply to the other compounds of other formulae. In the invention, alkyl and alkylene both may be a straight group or a branched group. The same shall apply to the cases where any hydrogen in these groups is replaced by halogen or a cyclic group and where any —CH$_2$— is replaced by —O—, —CH=CH—, cycloalkylene or cycloalkenylene. The word "any" as used herein is meant to indicate that not only position but also number may be selected freely. Plural hydrogens as well as (—CH$_2$—)'s may be replaced by different groups. For example, for the expression saying that "alkyl in which any —CH$_2$— may be replaced by —O— or —CH=CH—", the definition range of alkyl includes alkyl, alkoxy, alkenyl, alkenyloxy, alkoxyalkyl, alkoxyalkenyl, alkenyloxyalkyl, etc. In these, the alkoxy and the alkenylene in the alkoxyalkenyl, as well as the alkenyl and the alkylene in the alkenyloxyalkyl may be a straight group or a branched group. In the invention, when the description says that "any —CH$_2$— is replaced by —O—", then continuing plural (—CH$_2$—)'s are not replaced by —O—.

The PSQ derivative of the invention is represented by Formula (1).

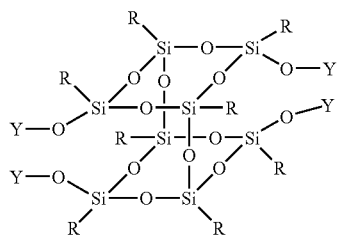

In Formula (1), each R is a group independently selected from hydrogen, alkyl having 1 to 45 carbon atoms, substituted or unsubstituted aryl, and substituted or unsubstituted arylalkyl. Preferably, all R's are the same group, but eight R's may be composed of at least two different groups.

Examples of the cases where eight R's are composed of different groups, include a case where they are composed of at least two alkyls, a case where they are composed of at least two aryls, a case where they are composed of at least two aralkyls, a case where they are composed of hydrogen and at least one aryl, a case where they are composed of at least one alkyl and at least one aryl, a case where they are composed of at least one alkyl and at least one arylalkyl, a case where they are composed of at least one aryl and at least one arylalkyl, etc. Any other combinations than these examples are acceptable herein. A method for producing a compound (1) having at least two different R's is described hereinunder.

When R is alkyl, it has 1 to 45 carbon atoms, but preferably 1 to 30 carbon atoms, more preferably 1 to 8 carbon atoms. Any hydrogen in the alkyl may be replaced by fluorine, and any —CH$_2$— may be replaced by —O—, —CH=CH—, cycloalkylene or cycloalkenylene. Preferred examples of the alkyl of the type are unsubstituted alkyl having 1 to 30 carbon atoms, alkoxyalkyl having 2 to 29 carbon atoms, alkyl having 1 to 8 carbon atoms in which one —CH$_2$— is replaced by cycloalkylene, alkenyl having 2 to 20 carbon atoms, alkenyloxyalkyl having 2 to 20 carbon atoms, alkyloxyalkenyl having 2 to 20 carbon atoms, alkyl having 1 to 8 carbon atoms in which one —CH$_2$— is replaced by cycloalkenylene, and the groups listed herein in which any hydrogen is replaced by fluorine. Preferably, cycloalkylene and cycloalkenylene have 3 to 8 carbon atoms, in which two carbons not adjacent to each other may be crosslinked.

Examples of unsubstituted alkyl having 1 to 30 carbon atoms are methyl, ethyl, propyl, 1-methylethyl, butyl, 2-methylpropyl, 1,1-dimethylethyl, pentyl, hexyl, 1,1,2-trimethylpropyl, heptyl, octyl, 2,4,4-trimethyl-pentyl, nonyl, decyl, undecyl, dodecyl, tetradecyl, hexadecyl, octadecyl, eicosyl, docosyl, and triacontyl.

Examples of fluoroalkyl having 1 to 30 carbon atoms are trifluoromethyl, 3,3,3-trifluoropropyl, nonafluoro-1,1,2,2-tetrahydrohexyl, tridecafluoro-1,1,2,2-tetrahydrooctyl, heptadecafluoro-1,1,2,2-tetrahydrodecyl, perfluoro-1H,1H,2H,2H-decyl, and perfluoro-1H,1H,2H,2H-tetradecyl.

Examples of alkoxyalkyl having 2 to 29 carbon atoms are 3-methoxypropyl, methoxyethoxyundecyl and 3-heptafluoroisopropoxypropyl.

Examples of alkyl having 1 to 8 carbon atoms in which one —CH$_2$— is replaced by cycloalkylene are cyclohexylmethyl, adamantylethyl, cyclopentyl, cyclohexyl, 2-bicycloheptyl and cyclooctyl. Cyclohexyl is an example of methyl in which —CH$_2$— is replaced by cyclohexylene. Cyclohexylmethyl is an example of ethyl in which —CH$_2$— is replaced by cyclohexylene.

Examples of alkenyl having 2 to 20 carbon atoms are vinyl, 2-propenyl, 3-butenyl, 5-hexenyl, 7-octenyl, 10-undecenyl and 21-docosenyl.

An example of alkenyloxyalkyl having 2 to 20 carbon atom is allyloxyundecyl.

Examples of alkyl having 1 to 8 carbon atoms in which one —CH$_2$— is replaced by cycloalkenylene are 2-(3-cyclohexenyl)ethyl, 5-(bicycloheptenyl)ethyl, 2-cyclopentenyl, 3-cyclohexenyl, 5-norbornen-2-yl and 4-cyclooctenyl.

Preferred examples of substituted or unsubstituted aryl for R in Formula (1) are phenyl in which any hydrogen may be replaced by halogen or alkyl having 1 to 10 carbon atoms, and naphthyl. Preferred examples of halogen are fluorine, chlorine and bromine. In the alkyl having 1 to 10 carbon atoms, any hydrogen may be replaced by fluorine and any —CH$_2$— may be replaced by —O—, —CH=CH— or phenylene. Concretely, preferred examples of substituted or unsubstituted aryl for R are phenyl, naphthyl, alkylphenyl, alkyloxyphenyl, alkenylphenyl, phenyl having a substituent of alkyl in which at least one —CH$_2$— may be replaced by phenylene, and the groups listed herein in which any hydrogen is replaced by halogen. The term "phenyl" as referred to herein with no specific indication is meant to indicate unsubstituted phenyl. Naphthyl is unsubstituted naphthyl.

Examples of halogenated phenyl are pentafluorophenyl, 4-chlorophenyl and 4-bromophenyl.

Examples of alkylphenyl are 4-methylphenyl, 4-ethylphenyl, 4-propylphenyl, 4-butylphenyl, 4-pentylphenyl, 4-heptylphenyl, 4-octylphenyl, 4-nonylphenyl, 4-decylphenyl, 2,4-dimethylphenyl, 2,4,6-trimethylphenyl, 2,4,6-triethylphenyl, 4-(1-methylethyl)phenyl, 4-(1,1-dimethylethyl)phenyl, 4-(2-ethylhexyl)phenyl and 2,4,6-tris(1-methylethyl)phenyl.

Examples of alkyloxyphenyl are 4-methoxyphenyl, 4-ethoxyphenyl, 4-propoxyphenyl, 4-butoxyphenyl, 4-pentyloxyphenyl, 4-heptyloxyphenyl, 4-decyloxyphenyl, 4-octadecyloxyphenyl, 4-(1-methylethoxy)phenyl, 4-(2-methylpropoxy)phenyl and 4-(1,1-dimethylethoxy)phenyl.

Examples of alkenylphenyl are 4-vinylphenyl, 4-(1-methylvinyl)phenyl and 4-(3-butenyl)phenyl.

Examples of phenyl in which at least one hydrogen is replaced by alkyl having 1 to 10 carbon atoms and at least one —CH$_2$— in the alkyl is replaced by phenylene are 4-(2-phenylvinyl)phenyl, 4-phenyloxyphenyl, 3-phenylmethylphenyl, biphenyl and terphenyl. 4-(2-phenylvinyl)phenyl is an example of ethylphenyl in which one —CH$_2$— in the ethyl group is replaced by phenylene and another —CH$_2$— is replaced by —CH=CH—.

Examples of phenyl in which a part of hydrogens are replaced by halogen and the other hydrogens are replaced by alkyl, alkyloxy or alkenyl are 3-chloro-4-methylphenyl, 2,5-dichloro-4-methylphenyl, 3,5-dichloro-4-methylphenyl, 2,3,5-trichloro-4-methylphenyl, 2,3,6-trichloro-4-methylphenyl, 3-bromo-4-methylphenyl, 2,5-dibromo-4-methylphenyl, 3,5-dibromo-4-methylphenyl, 2,3-difluoro-4-methylphenyl, 3-chloro-4-methoxyphenyl, 3-bromo-4-methoxyphenyl, 3,5-dibromo-4-methoxyphenyl, 2,3-difluoro-4-methoxyphenyl, 2,3-difluoro-4-ethoxyphenyl, 2,3-difluoro-4-propoxyphenyl and 4-vinyl-2,3,5,6-tetrafluorophenyl.

Examples of Formula (1) where R is substituted or unsubstituted arylalkyl are described. In the alkylene group of arylalkyl, any hydrogen may be replaced by fluorine and any —CH$_2$— may be replaced by —O—, —CH=CH— or cycloalkylene. A preferred example of arylalkyl is phenylalkyl. In this, any hydrogen in the phenyl group may be replaced by halogen or alkyl having 1 to 10 carbon atoms. In the alkyl having 1 to 10 carbon atoms, any hydrogen may be replaced by fluorine and any —CH$_2$— may be replaced by —O—, —CH=CH—, cycloalkylene or phenylene. Preferably, the alkylene group has 1 to 12 carbon atoms, more preferably from 1 to 8 carbon atoms.

Examples of unsubstituted phenylalkyl are phenylmethyl, 2-phenylethyl, 3-phenylpropyl, 4-phenylbutyl, 5-phenylpentyl, 6-phenylhexyl, 11-phenylundecyl, 1-phenylethyl, 2-phenylpropyl, 1-methyl-2-phenylethyl, 1-phenylpropyl, 3-phenylbutyl, 1-methyl-3-phenylpropyl, 2-phenylbutyl, 2-methyl-2-phenylpropyl and 1-phenylhexyl.

Examples of phenylalkyl in which at least one hydrogen in the phenyl group is replaced by fluorine are 4-fluorophenylmethyl, 2,3,4,5,6-pentafluorophenylmethyl, 2-(2,3,4,5,6-pentafluorophenyl)ethyl, 3-(2,3,4,5,6-pentafluorophenyl)propyl, 2-(2-fluorophenyl)propyl, and 2-(4-fluorophenyl)propyl.

Examples of phenylalkyl in which at least one hydrogen in the phenyl group is replaced by chlorine are 4-chlorophenylmethyl, 2-chlorophenylmethyl, 2,6-dichlorophenylmethyl, 2,4-dichlorophenylmethyl, 2,3,6-trichlorophenylmethyl, 2,4,6-trichlorophenylmethyl, 2,4,5-trichlorophenylmethyl, 2,3,4,6-tetrachlorophenyl-methyl, 2,3,4,5,6-pentachlorophenylmethyl, 2-(2-chlorophenyl)ethyl, 2-(4-chlorophenyl)ethyl, 2-(2,4,5-chlorophenyl)ethyl, 2-(2,3,6-chlorophenyl)ethyl, 3-(3-chlorophenyl)propyl, 3-(4-chlorophenyl)propyl, 3-(2,4,5-trichlorophenyl)propyl, 3-(2,3,6-trichlorophenyl)propyl, 4-(2-chlorophenyl)butyl, 4-(3-chlorophenyl)butyl, 4-(4-chlorophenyl)butyl, 4-(2,3,6-trichlorophenyl)butyl, 4-(2,4,5-trichlorophenyl)butyl, 1-(3-chlorophenyl)ethyl, 1-(4-chlorophenyl)ethyl, 2-(4-chlorophenyl)propyl, 2-(2-chlorophenyl)propyl, and 1-(4-chlorophenyl)butyl.

Examples of phenylalkyl in which at least one hydrogen in the phenyl group is replaced by bromine are 2-bromophenylmethyl, 4-bromophenylmethyl, 2,4-dibromophenylmethyl, 2,4,6-tribromophenylmethyl, 2,3,4,5-tetrabromophenylmethyl, 2,3,4,5,6-pentabromophenylmethyl, 2-(4-bromophenyl)ethyl, 3-(4-bromophenyl)propyl, 3-(3-bromophenyl)propyl, 4-(4-bromophenyl)butyl, 1-(4-bromophenyl)ethyl, 2-(2-bromophenyl)propyl, and 2-(4-bromophenyl)propyl.

Examples of phenylalkyl in which at least one hydrogen in the phenyl group is replaced by alkyl having 1 to 10 carbon atoms are 2-methylphenylmethyl, 3-methylphenylmethyl, 4-methylphenylmethyl, 4-decylphenylmethyl, 3,5-dimethylphenylmethyl, 2-(4-methylphenyl)ethyl, 2-(3-methylphenyl)ethyl, 2-(2,5-dimethylphenyl)ethyl, 2-(4-ethylphenyl)ethyl, 2-(3-ethylphenyl)ethyl, 1-(4-methylphenyl)ethyl, 1-(3-methylphenyl)ethyl, 1-(2-methylphenyl)ethyl, 2-(4-methylphenyl)propyl, 2-(2-methylphenyl)propyl, 2-(4-ethylphenyl)propyl, 2-(2-ethylphenyl)propyl, 2-(2,3-dimethylphenyl)propyl, 2-(2,5-dimethylphenyl)propyl, 2-(3,5-dimethylphenyl)propyl, 2-(2,4-dimethylphenyl)propyl, 2-(3,4-dimethylphenyl)propyl, 2-(2,5-dimethylphenyl)butyl, 4-(1-methylethyl)phenylmethyl, 2-(4-(1,1-dimethylethyl)phenyl)ethyl, 2-(4-(1-methylethyl)phenyl)propyl, and 2-(3-(1-methylethyl)phenyl)propyl.

Examples of phenylalkyl in which at least one hydrogen in the phenyl group is replaced by alkyl having 1 to 10 carbon atoms and the hydrogen of the alkyl is replaced by fluorine are 3-trifluoromethylphenylmethyl, 2-(4-trifluoromethylphenyl)ethyl, 2-(4-nonafluorobutylphenyl)ethyl, 2-(4-tridecafluorohexylphenyl)ethyl, 2-(4-heptadecafluorooctylphenyl)ethyl, 1-(3-trifluoromethylphenyl)ethyl, 1-(4-trifluoromethylphenyl)ethyl, 1-(4-nonafluorobutylphenyl)ethyl, 1-(4-tridecafluorohexylphenyl)ethyl, 1-(4-heptadecafluorooctylphenyl)ethyl, 2-(4-nonafluorobutylphenyl)propyl, 1-methyl-1-(4-nonafluorobutylphenyl)ethyl, 2-(4-tridecafluorohexylphenyl)propyl, 1-methyl-1-(4-tridecafluorohexylphenyl)ethyl, 2-(4-heptadecafluorooctylphenyl)propyl, and 1-methyl-1-(4-heptadecafluorooctylphenyl)ethyl.

Examples of phenylalkyl in which at least one hydrogen in the phenyl group is replaced by alkyl having 1 to 10 carbon atoms and —CH$_2$— in the alkyl is replaced by —CH=CH— are 2-(4-vinylphenyl)ethyl, 1-(4-vinylphenyl)ethyl, and 1-(2-(2-propenyl)phenyl)ethyl.

Examples of phenylalkyl in which at least one hydrogen in the phenyl group is replaced by alkyl having 1 to 10 carbon atoms and —CH$_2$— in the alkyl is replaced by —O— are 4-methoxyphenylmethyl, 3-methoxyphenylmethyl, 4-ethoxyphenylmethyl, 2-(4-methoxyphenyl)ethyl, 3-(4-methoxyphenyl)propyl, 3-(2-methoxyphenyl)propyl, 3-(3,4-dimethoxyphenyl)propyl, 11-(4-methoxyphenyl)undecyl, 1-(4-methoxyphenyl)ethyl, (3-methoxymethylphenyl)ethyl, and 3-(2-nonadecafluorodecenyloxyphenyl)propyl.

Examples of phenylalkyl in which at least one hydrogen in the phenyl group is replaced by alkyl having 1 to 10 carbon atoms and —CH$_2$— in the alkyl is replaced by cycloalkylene (and —O—) are cyclopentylphenylmethyl, cyclopentyloxyphenylmethyl, cyclohexylphenylmethyl, cyclohexylphenylethyl, cyclohexylphenylpropyl, and cyclohexyloxyphenylmethyl.

Examples of phenylalkyl in which at least one hydrogen in the phenyl group is replaced by alkyl having 1 to 10 carbon atoms and —CH$_2$— in the alkyl is replaced by phenylene (and —O—) are 2-(4-phenoxyphenyl)ethyl, 2-(4-phenoxyphenyl)propyl, 2-(2-phenoxyphenyl)propyl, 4-biphenylylmethyl, 3-biphenylylethyl, 4-biphenylylethyl, 4-biphenylylpropyl, 2-(2-biphenylyl)propyl, and 2-(4-biphenylyl)propyl.

Examples of phenylalkyl in which at least two hydrogens in the phenyl group are replaced by different groups are 3-(2,5-dimethoxy-3,4,6-trimethylphenyl)propyl, 3-chloro-2-methylphenylmethyl, 4-chloro-2-methylphenylmethyl, 5-chloro-2-methylphenylmethyl, 6-chloro-2-methylphenylmethyl, 2-chloro-4-methylphenylmethyl, 3-chloro-4-methylphenylmethyl, 2,3-dichloro-4-methylphenylmethyl, 2,5-dichloro-4-methylphenylmethyl, 3,5-dichloro-4-methylphenylmethyl, 2,3,5-trichloro-4-methylphenylmethyl, 2,3,5,6-tetrachloro-4-methylphenylmethyl, 2,3,4,6-tetrachloro-5-methylphenylmethyl, 2,3,4,5-tetrachloro-6-methylphenyl, 4-chloro-3,5-dimethylphenylmethyl, 2-chloro-3,5-dimethylphenylmethyl, 2,4-dichloro-3,5-dimethylphenyl-methyl, 2,6-dichloro-3,5-dimethylphenylmethyl, 2,4,6-trichloro-3,5-dimethylphenylmethyl, 3-bromo-2-methylphenylmethyl, 4-bromo-2-methylphenylmethyl, 5-bromo-2-methylphenylmethyl, 6-bromo-2-methylphenylmethyl, 3-bromo-4-methylphenylmethyl, 2,3-dibromo-4-methylphenyl-methyl, 2,3,5-tribromo-4-methylphenylmethyl, 2,3,5,6-tetrabromo-4-methylphenylmethyl, and 11-(3-chloro-4-methoxyphenyl)undecyl.

Most preferred examples of the phenyl group in phenylalkyl are an unsubstituted phenyl group, and a phenyl group having at least one of fluorine alkyl having 1 to 4 carbon atoms, vinyl and methoxy as a substituent. Examples of phenylalkyl in which —CH₂— in the alkylene group is replaced by —O—, —CH=CH— or cycloalkylene are 3-phenoxypropyl, 1-phenylvinyl, 2-phenylvinyl, 3-phenyl-2-propenyl, 4-phenyl-4-pentenyl, 13-phenyl-12-tridecenyl, phenylcyclohexyl, and phenoxycyclohexyl.

Examples of phenylalkyl in which hydrogen in the phenyl group is replaced by fluorine or methyl are 4-fluorophenylvinyl, 2,3-difluorophenylvinyl, 2,3,4,5,6-pentafluorophenylvinyl, and 4-methylphenylvinyl.

Of those groups, preferred examples of R are groups selected from alkyl having 1 to 8 carbon atoms in which any hydrogen may be replaced by fluorine and any —CH₂— may be replaced by —O—, —CH=CH—, cycloalkylene or cycloalkenylene, phenyl in which any hydrogen may be replaced by halogen, methyl or methoxy, phenylalkyl composed of a phenyl group in which any hydrogen may be replaced by fluorine, alkyl having 1 to 4 carbon atoms, vinyl or methoxy, and an alkylene group having 1 to 8 carbon atoms in which any —CH₂— may be replaced by —O—, —CH=CH— or cycloalkylene, and naphthyl. More preferred examples of R are groups selected from the group of phenyl, the group of phenylalkyl, and naphthyl, listed herein. When the phenyl group in phenyl or phenylalkyl has plural substituents, then the substituents may be the same group or different groups. Preferably, all R's in Formula (1) are the same group selected from the preferred examples.

More preferred examples of R are phenyl, halogenated phenyl, phenyl having at least one methyl, methoxyphenyl, naphthyl, phenylmethyl, phenylethyl, phenylbutyl, 2-phenylpropyl, 1-methyl-2-phenylethyl, pentafluorophenylpropyl, 4-ethylphenylethyl, 3-ethylphenylethyl, 4-(1,1-dimethylethyl)phenylethyl, 4-vinylphenylethyl, 1-(4-vinylphenyl)ethyl, 4-methoxyphenylpropyl and phenoxypropyl. Of those examples, phenyl is most preferred.

Y in Formula (1) is described. At least one Y is a group selected from the group represented by Formula (2), and the other Y is hydrogen. When at least two Y's are a group represented by Formula (2), then they may be the same group or may be composed of at least two different groups.

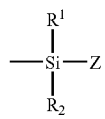
(2)

In Formula (2), R¹ and R² are independently a group defined similarly to R in Formula (1). Preferred examples of R¹ and R² are methyl, isopropyl, tert-butyl and phenyl.

Z in Formula (2) is a group defined similarly to R in Formula (1), or a functional group, or a group having a functional group. Of the group defined similarly to R, preferred for Z are alkyl having 1 to 45 carbon atoms, phenyl in which any hydrogen of the benzene ring may be replaced by halogen or alkyl having 1 to 10 carbon atoms, and naphthyl. Preferred examples of these groups are the same as those mentioned hereinabove for R.

Preferred examples of Z are a functional group, or a group having a functional group. Preferred examples of the functional group are hydrogen (directly bonding to the Si atom), halogen, —OH, fluoroalkyl, alkoxy, carboxyl, 2-oxapropanedioyl, —COO—, —OCO—, polyalkyleneoxy, oxiranyl, 3,4-epoxycyclohexyl, oxetanyl, oxetanylene, alkenyl, cycloalkenyl, —NH₂, —NH—, —CN, —NCO, —SH and —PH₂.

Halogen, —OH, alkoxy, alkenyl, and trifluoromethyl of fluoroalkyl may directly bond to the Si atom, or may bond to the Si atom via a divalent group mentioned below. The other groups than hydrogen, halogen, —OH, trifluoromethyl, alkoxy and alkenyl preferably bond to the Si atom via a divalent group such as alkylene, alkylcycloalkylene, alkylphenylene, alkylcycloalkylene or alkylphenylalkylene. Examples of halogen are fluorine, chlorine and bromine. Examples of alkenyl are vinyl and allyl. Examples of cycloalkenyl are cyclopentadienyl, cyclohexenyl and norbornenyl.

More preferred examples of the functional group are hydrogen (directly bonding to Si), halogen, —OH, carboxyl, 2-oxapropanedioyl, oxiranyl, 3,4-epoxycyclohexyl, oxetanyl, oxetanylene, alkenyl and —NH₂. The group having halogen is halogenated alkyl, halogenated phenyl, halogenated alkylphenyl, and halogen directly bonding to the Si atom. These preferred functional groups can be utilized for leading them into other functional groups, and can be utilized when the compound (1) is used as a starting material of polymer.

Preferred examples of Z are concretely listed below.

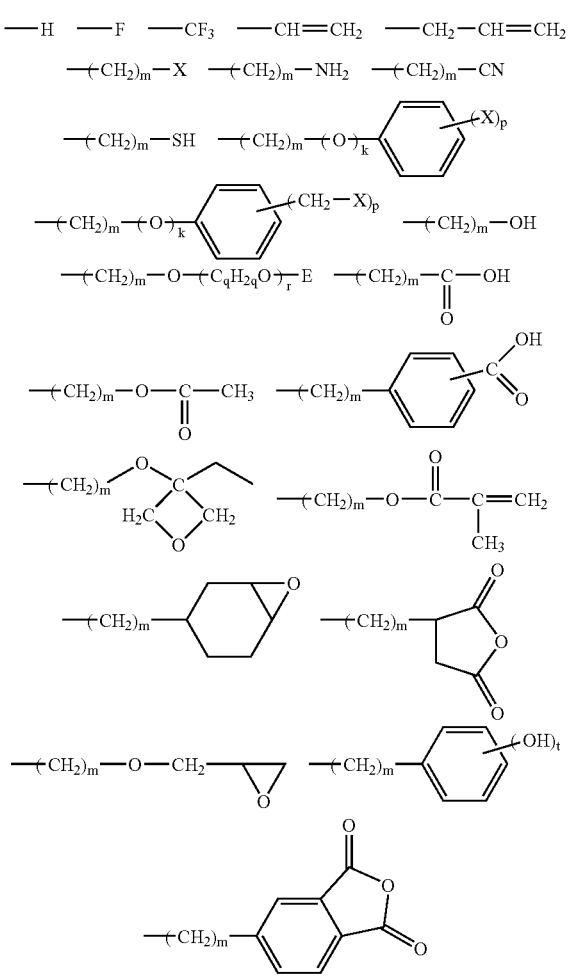

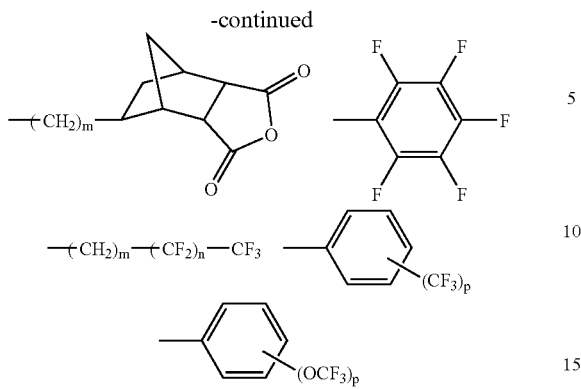

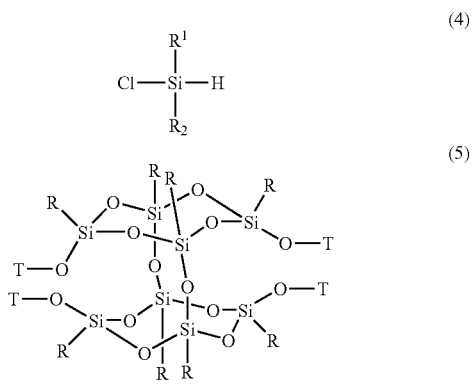

In these formulae, k is 0 or 1; m is an integer of 1 to 4; n is an integer of 0 to 15. X is halogen; p is an integer of 1 to 5. q is 2 or 3; r is an integer of 2 to 200. t is an integer of 1 to 3. E is hydrogen, or alkyl having 1 to 4 carbon atoms. In the above-mentioned examples, —X, —CH$_2$, —X, —OH, —COOH, —CF$_3$ and —OCF$_3$ may bond to the benzene ring at any position. Preferred halogens are fluorine and chlorine. A preferred range of r is 2 to 100. More preferably, it is 2 to 20.

A method for producing a compound (1) is described below. A compound (1) can be readily produced from a compound (3). The compound (3) can be readily produced at high yield by hydrolyzing and polycondensing a silicon compound having three hydrolyzable groups, in the presence of an alkali metal hydroxide in an oxygen-containing organic solvent such as tetrahydrofuran (hereinafter referred to as THF) or alcohol. Many silicon compounds having three hydrolyzable groups are commercially available. Commercially-unavailable compounds can be synthesized in known techniques (e.g., reaction of halogenated silane and Grignard reagent).

When at least two silicon compounds having three hydrolyzable groups are used in producing a compound (3), then a compound (3), which eight R's in Formula (3) are composed of at least two different groups, can be obtained.

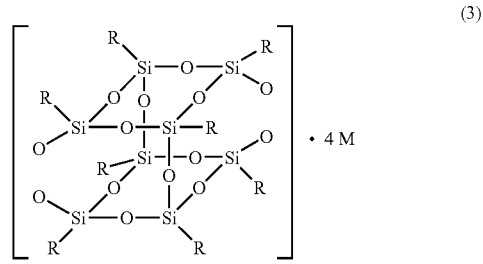

In Formula (3), R has the same meaning as R in Formula (1); M is a monovalent alkali metal atom. Examples of the alkali metal atom are lithium, potassium, sodium, cesium; and sodium is preferred.

One method of producing a compound (1) from a compound (3) comprises reacting a compound (3) with a compound (4) to give a compound (5), and hydrosilylating it with a compound having a functional group and an unsaturated hydrocarbon group.

In Formula (4), R$^1$ and R$^2$ have the same meanings as those in Formula (2). In Formula (5), at least one T is the following group that is derived from Formula (4) by removing Cl, and the other T is hydrogen.

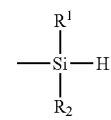

The compound (4) is a chlorosilane, but any other halogenated silane may also be used in the same manner as herein. Some compounds (4) are commercially available. Commercially-unavailable compounds (4) can be readily obtained, known technique, for example, according to a method of reacting a halogenated silane with a Grignard reagent. In view of the easy availability thereof, preferred examples of the compound (4) are dimethylchlorosilane, diethylchlorosilane, methylethylchlorosilane, methylhexylchlorosilane, diisopropylchlorosilane, di-tert-butylchlorosilane, dichcloropentylchclorosilane, dicyclohexylchlorosilane, di-n-octylchlorosilane, methylphenylchlorosilane and diphenylchlorosilane.

Preferably, an organic solvent is used in the reaction of a compound (3) and a compound (4). Specifically, a compound (3) is mixed in an organic solvent, and a compound (4) is dropwise added to the resulting mixture. After the reaction, if desired, the compound (4) is removed through distillation, and then water is added to the system in which the by-product, alkali metal chloride is thereby dissolved. Then, the organic layer is washed with water, and dried with a dehydrating agent. Next, the solvent is evaporated away from the organic layer to obtain Compound (5). If desired, the compound (5) may be recrystallized or may be subjected to impurity extraction with organic solvent to thereby increase the purity thereof.

The solvent to be used for the reaction is selected under the condition that it does not interfere with the reaction process, and there is no specific limitation thereon except it. Preferred solvents are aliphatic hydrocarbons (e.g., hexane, heptane), aromatic hydrocarbons (e.g., benzene, toluene, xylene), ethers (e.g., diethyl ether, THF, 1,4-dioxane), halogenated hydrocarbons (e.g., methylene chloride, carbon tetrachloride), and esters (e.g., ethyl acetate). One or more of these solvents may be used herein either singly or as combined. More preferred solvents are aromatic hydrocarbons and ethers; and even more preferred solvents are toluene and THF. It is desirable that the content of impurities (e.g., water) that readily react with a compound (4) is as small as possible in the solvent.

The preferred ratio of the compound (3) to be mixed in solvent may fall between 0.05 and 50% by weight based on the weight of the solvent. In order that the concentration of the by-product salt does not so increase as to interfere with the reaction process, it is desirable that the ratio is at most 50% by weight. In order that the volume efficiency does not so worsen as to have some negative influence on the production cost, it is desirable that the ratio is at least 0.05% by weight. More preferably, the ratio falls between 1 and 10% by weight. There is no specific limitation on the amount of Compound (4) to be used except that it is at least 4 in terms of the molar ratio to the compound (3). However, in consideration of the post-processing step, it is undesirable to use a large excess amount of the compound. Regarding the ratio of the compound (4) to be used to the compound (3), when a part of T's are to still remain as —H, the molar ratio may be smaller than 4. On the other hand, when the reactivity of the compound (4) is low, then a compound (5) in which a part of T's are still hydrogen may be obtained even though the molar ratio of the compound used is 4 or more. The reaction temperature may be room temperature, but, if desired, the system may be heated so as to promote the reaction. On the other hand, when reaction heat must be removed or when any undesirable reaction must be controlled, then the reaction system may be cooled.

The reaction may be readily promoted by adding a compound having an amino group such as triethylamine, or a basic organic compound is added to the system. A preferred ratio of triethylamine or the like additive to the system is described. When triethylamine is used, its amount may be 0.005 to 10% by weight based on the weight of the solvent, more preferably 0.01 to 3% by weight. However, since triethylamine is enough so far as it may readily promote the reaction, there is no specific limitation on its amount to be added to the system.

The resulting compound (5) is hydrosilylated with a compound having a functional group and an unsaturated hydrocarbon group to thereby produce a compound (1). Examples of the unsaturated hydrocarbon group are alkenyl having 2 to 30 carbon atoms, alkynyl having 2 to 30 carbon atoms, arylalkenyl having 6 to 10 carbon atoms, and arylalkynyl having 6 to 10 carbon atoms. Concretely, they are vinyl, allyl, isopropenyl, 3-butenyl, 2,4-pentadienyl, butadienyl, 5-hexenyl, undecenyl, ethynyl, propynyl, hexynyl, cyclopentenyl, cyclohexenyl, 3-cyclohexenylethyl, 5-bicycloheptenyl, norbornenyl, 4-cyclooctenyl, cyclooctadienyl, styryl, styrylethyl, styryloxy, allyloxypropyl, 1-methoxyvinyl, cyclopentenyloxy, 3-cyclohexenyloxy, acryloyl, acryloyloxy, methacryloyl, methacryloyloxy.

Examples of the compound having an epoxy group and an unsaturated hydrocarbon group are ally glycidyl ether, 2-methylallyl glycidyl ether, vinyl glycidyl ether, glycidyl maleate, glycidyl itaconate, glycidyl acrylate, glycidyl methacrylate, 2,6-dimethyl-2,3-epoxy-7-octene, 1,2-epoxy-6-heptene, 1,2-epoxy-3-butene, 2-cyclohexyene-1-glycidyl ether, cyclohexene-4,5-diglycidyl carboxylate, cyclohexene-4-glycidyl carboxylate, 5-norbornene-2-methyl-2-glycidyl carboxylate, endocis-bicyclo[2.2.1]-5-heptene-2,3-diglycidyl dicarboxylate, 1-methyl-4-isopropenylcyclohexeneoxide, 1,4-dimethyl-4-vinylcyclohexeneoxide, 4-vinylcyclohexeneoxide, vinylnorbornene-monoxide, and dicyclopentadiene-monoxide. In view of the easy availability thereof, preferred are 4-vinylcyclohexaneoxide and allyl glycidyl ether.

Examples of the compound having —OH and an unsaturated hydrocarbon group are allyl alcohol, 3-buten-1-ol, 3-buten-2-ol, ethylene glycol monovinyl ether, ethylene glycol monoallyl ether, diethylene glycol monoallyl ether, glycerin monoallyl ether, trimethylolethane monoallyl ether, trimethylolpropane monoallyl ether, polyethylene glycol monoallyl ether, polypropylene glycol monoallyl ether, 1-vinylcyclobutanol, 2-vinylcyclobutanol, 3-vinylcyclobutanol, vinylphenol, 2-allylphenol, 4-allylphenol, 4-allyl-2-methoxyphenol, 4-allyl-2,6-dimethoxyphenol, 4-(2-propenyl)-1,2-benzenediol, and 4-(2,4-dihydroxyphenyl)-3-buten-2-one. —OH in these compounds may be protected through esterification, acetalization, ketalization or silyletherification. In view of the easy availability thereof, preferred compounds of those are allyl alcohol, ethylene glycol monoallyl ether, glycerin monoallyl ether, trimethylolpropane monoallyl ether, 2-allylphenol and 4-allylphenol.

Examples of the compound having a mercapto group and an unsaturated hydrocarbon group are allylmercaptan and 2-methyl-2-propene-1-thiol.

Examples of the compound having a carboxyl group and an unsaturated hydrocarbon group are (meth)acrylic acid, crotonic acid, isocrotonic acid, 3-butenoic acid, 2-methyl-3-butenoic acid, 2,2-dimethyl-3-butenoic acid, 2-n-propyl-3-pentenoic acid, 4-pentenoic acid, 3-methyl-4-pentenoic acid, 2,2-dimethyl-4-pentenoic acid, 3,3-dimethyl-4-pentenoic acid, 4-hexanoic acid, 5-hexenoic acid, 2,6-heptadienoic acid, 7-octenoic acid, 8-nonenoic acid, 9-decenoic acid, 10-undecenoic acid, 11-dodecenoic acid, propiolic acid, 2-butynoic acid, maleic acid, fumaric acid, acetylenecarboxylic acid, 2-vinylbenzoic acid, 3-vinylbenzoic acid, 4-vinylbenzoic acid, and 4-allyl-2,3,5,6-tetrafluorobenzoic acid. (Meth)acrylic acid indicates acrylic acid and methacrylic acid. The carboxyl group in these compound may be protected through esterification or trialkylsilylation. In view of the easy availability thereof, preferred compounds of these are (meth)acrylic acid, 4-pentenoic acid, 10-undecenoic acid and 4-vinylbenzoic acid.

Examples of the compound having a 2-oxapropanedioyl group and an unsaturated hydrocarbon group are allylsuccinic anhydride, isobutylsuccinic anhydride, isobutenylsuccinic anhydride, bicyclo[2.2.2]oct-7-ene-2,3,5,6-tetracarboxylic dianhydride, and 5-norbornene-2,3-dicarboxylic anhydride. In view of the easy availability thereof, preferred examples of these are allylsuccinic anhydride and 5-norbornene-2,3-dicarboxylic anhydride.

Examples of the compound having a perfluoroalkyl group and an unsaturated hydrocarbon group are $C_2F_5CH=CH_2$, n-$C_4F_9CH=CH_2$, n-$C_6F_{13}CH=CH_2$, n-$C_8F_{17}CH=CH_2$, n-$C_{10}F_{21}CH=CH_2$, n-$C_{12}F_{25}CH=CH_2$, n-$C_{14}F_{29}CH=CH_2$, n-$C_6F_{13}CH_2CH_2CH=CH_2$, pentafluoropropyl methacrylate, tetrafluoropropyl methacrylate, heptafluorobutyl methacrylate, octafluoropentyl methacrylate, and hexadecafluorononyl methacrylate.

Examples of the compound having a (meth)acryloyl group and an unsaturated hydrocarbon group are allyl (meth)acrylate, 2-butenyl (meth)acrylate, 3-methyl-3-butenyl (meth)acrylate, 3-methyl-2-butenyl (meth)acrylate, cyclohexenylmethyl (meth)acrylate, 2-methyl-2-propenyl (meth)acrylate, 3-heptenyl (meth)acrylate, 4-hexenyl (meth)acrylate, and 2-hydroxyethyl methacrylate/vinylcyclohexene-monoepoxide (1/1) adduct. (Meth)acryloyl indicates acryloyl or methacryloyl. (Meth)acrylate indicates acrylate or methacrylate. These acrylic compounds may be produced, for example, through reaction of a (meth)acrylic acid chloride and an alkenyl alcohol, interesterification of an alkyl (meth)acrylate with an alkenyl alcohol, or addition reaction of an alkenyl alcohol to an isocyanate group-containing acrylic monomer.

Examples of the compound having a cyano group and an unsaturated hydrocarbon group are acrylonitrile, allylcyanide, methacrylonitrile, crotononitrile, 3-methylcrotononitrile, ethylacrylonitrile, 2-butenenitrile, 2-methyl-3-butenenitrile, 4-methyl-3-pentenenitrile, and 5-hexenenitrile. In consideration of the easy availability thereof, preferred compounds of these are acrylonitrile, allylcyanide and methacrylonitrile.

Examples of the compound having an isocyanate group and an unsaturated hydrocarbon group are vinyl isocyanate, allyl isocyanate, 3-isocyanato-2-methyl-2-propene, methacryloyl isocyanate, isocyanatoethyl methacrylate, vinylbenzyl isocyanate, 3-isocyanato-1-butene, 3-isocyanato-3-methyl-1-butene, 4-isocyanato-2-methyl-1-butene, 4-isocyanato-3,3-dimethyl-1-butene, 4-isocyanato-4-methyl-1-pentene, and 5-isocyanato-1-pentene. In consideration of the easy availability thereof, preferred compounds of these are vinyl isocyanate, allyl isocyanate, and methacryloyl isocyanate.

Compounds having an alkyleneoxy group and an unsaturated hydrocarbon group are put on the market by Nippon Yushi, etc. For example, examples of polyethylene glycol monoallyl ether are PKA-5001, PKA-5002, PKA-5003, PKA-5004, and PKA 5005. Examples of methoxypolyethylene glycol allyl ether are PKA-5006, PKA-5007, PKA-5008, PKA-5009, and PKA-5010. An example of polypropylene glycol monoallyl ether is PKA-5014. Examples of polyethylene glycol-polypropylene glycol allyl ether are PKA-5011, PKA-5012, and PKA-5013. When commercially unavailable, allyl ethers having an alkyleneoxy group can be obtained by reacting a polyalkylene glycol or its monoether compound with sodium hydride to give a sodium alcoholate followed by reacting it with an allyl bromide.

The compound (5) is hydrosilylated with one selected from the above-mentioned compounds having a functional group and an unsaturated hydrocarbon group, and a compound (1) having the same functional group is thereby obtained. For producing a compound (1) having at least two different functional groups, at least two compounds having a functional group and an unsaturated hydrocarbon group shall be reacted with a compound (5). For obtaining a compound (1) in which some Z's are a group having a functional group and some others are R, a mixture of a compound having a functional group and an unsaturated hydrocarbon group, and a compound having R not having a functional group, and an unsaturated hydrocarbon group shall be reacted with a compound (5). In this case, the compounds to constitute the mixture may be reacted with a compound (5) all at a time as their mixture, or may be reacted one by one with it. In the latter case of successive reaction, the reactivity of the functional group may interfere with the reaction, and if so, the functional group may be previously protected with a protective group such as trimethylsilyl.

When the number of the functional groups in the compound (1) is desired to be 1 to 3, a compound (5) having functional groups of Si—H and Si—OH can be obtained by reacting a compound (4) in a molar ratio of 1 to 3 for a compound (3) with this compound. Therefore, this method is inconvenient for obtaining a compound (1) having 1 to 3 functional groups of one and the same type. For attaining the object, a mixture of a compound represented by Formula (4) and another compound of Formula (4) in which H is replaced by R shall be reacted with a compound (3). Another method comprises reacting a compound (4) with a compound (3) in such a controlled manner that the resulting product has no Si—OH remaining therein. In this case, a compound (5) having four (Si—H)'s is obtained, and a mixture of a compound having a functional group and an unsaturated hydrocarbon group and another compound not having a functional group but having an unsaturated hydrocarbon group alone may be reacted with the compound (5) of the type.

The solvent to be used in the hydrosilylation is selected under the condition that it does not interfere with the reaction process, and except this, there is no specific limitation on the solvent. Preferred examples of the solvent may be the same as those of the solvent to be used in the reaction of a compound (3) and a compound (4). One or more of such solvents may be used either singly or as combined. More preferred solvents are aromatic hydrocarbons, of which toluene is the best.

When a compound (5) is reacted with a compound having a functional group and an unsaturated hydrocarbon group, a preferred ratio of the compound (5) to the solvent is 0.05 to 80% by weight on the basis of the weight of the solvent. A more preferred ratio is 30 to 70% by weight. The amount of the compound having a functional group and an unsaturated hydrocarbon group to be used relative to the compound (5) varies, depending on the object. When the compound is reacted with all of four Si—H groups, then the preferred molar ratio of the compound is at least 4 to the compound (5) for increasing the yield of the product. When different functional groups are introduced into the product, or when a mixture of a compound having a functional group and an unsaturated hydrocarbon group and another compound not having a functional group but having R and an unsaturated hydrocarbon group is reacted with a compound (5), the total amount of the compounds to be used must be in a molar ratio of at least 4 in order that no Si—H group could remain in the product. On the other hand, when the product is to have some (Si—H) groups remaining therein, then the total amount of the compounds to be used having an unsaturated hydrocarbon group shall be in a molar ratio of smaller than 4 to the compound (5). When the number of Si—H groups in a compound (5) is smaller than 4, the same consideration as above shall be given to the reaction depending on the number of the groups in the compound.

The reaction temperature may be room temperature. For promoting the reaction, if desired, the system may be heated. On the other hand, when reaction heat must be removed or when any undesirable reaction must be controlled, then the reaction system may be cooled. Also if desired, a hydrosilylation catalyst may be added to the system to attain more smooth reaction. Preferred examples of the hydrosilylation catalyst are Karstedt catalyst, Spier catalyst and Wilkinson catalyst, and these are well-known catalysts.

Since these hydrosilylation catalysts have high reactivity, adding only a small amount of the catalyst may sufficiently promote the reaction. In general, the amount of the catalyst to be used may be controlled within a range where the transition metal in the catalyst may be $10^{-9}$ to 1 mol % of the hydrosilyl group. A preferred amount of the catalyst is $10^{-7}$ to $10^{-3}$ mol %. The amount of the catalyst necessary for promoting the reaction and for completing the reaction within an acceptable period of time is such that the transition metal contained in the catalyst could be at least $10^{-9}$ mol % relative to the hydrosilyl group. Taking the matter into consideration that the production costs are reduced, the amount of the catalyst to be added must be so controlled that the transition metal contained in the catalyst could be at most 1 mol % relative to the hydrosilyl group.

Another method of producing a compound (1) from a compound (3) comprises reacting a compound (3) with a compound (6). Some compounds (6) are commercially available. Commercially-unavailable compounds (6) may be produced according to known techniques, for example, according to a method of reacting a halogenated silane with a Grignard reagent, or a method reacting a halogenated hydrosilane and an unsaturated hydrocarbon having a functional group for hydrosilylation.

(6)

The methods are effective also for commercially-available compounds (6).

Basically, the reaction may be attained completely in the same manner as that for the reaction of a compound (3) and a compound (4). A preferred amount of Compound (6) to be used is in a molar ratio of at least 4 to the compound (3) for increasing the reaction yield. When one compound (6) is reacted with a compound (3), then a compound (1) having the same functional group may be obtained. For producing a compound (1) having at least two different functional groups, at least two compounds (6) shall be reacted with a compound (3). For obtaining a compound (1) in which some Z's are a group having a functional group and some others are R, a mixture of a compound (6) and another compound of Formula (6) in which Z is R shall be reacted with a compound (3). In this case, the difference in the reactivity between the compounds (6) is taken into consideration, and the compounds (6) to constitute the mixture may be reacted with a compound (3) all at a time as their mixture, or may be reacted one by one with it. In the latter case of successive reaction, the reactivity of the functional group may interfere with the reaction, and if so, the functional group may be previously protected with a protective group such as trimethylsilyl. When at least two compounds (6) are used, then the total amount of the compounds to be used shall be in a molar ratio of at least 4 to the compound (3). If the molar ratio is smaller than 4, or if the reactivity of the compound (6) is low, then a compound (1) in which some Y's are hydrogen can be obtained.

Examples of the compound (6) are acetoxyethyldimethylchlorosilane, 3-acetoxypropyldimethylchlorosilane, 3-(trimethylsiloxy)propyldimethylchlorosilane, 10-(carbomethoxy)decyldimethylchlorosilane, chloromethyldimethylchlorosilane, chloromethylmethylchlorosilane, dichloromethyldimethylchlorosilane, bis(chloromethyl)methylchlorosilane, bromomethyldimethylchlorosilane, 3-chloropropyldimethylchlorosilane, 4-chlorobutyldimethylchlorosilane, 11-bromoundecyldimethylchlorosilane, ((chloromethyl)phenylethyl)dimethylchlorosilane, 3-cyanopropyldimethylchlorosilane, 3-cyanopropyldiisopropylchlorosilane, vinyldimethylchlorosilane, allyldimethylsilane, 5-hexenyldimehtylchlorosilane, 7-octenyldimethylchlorosilane, 10-undecenyldimethylchlorosilane, vinylphenylmethylchlorosilane, vinyldiphenylchlorosilane, phenylethynyldiisopropylchlorosilane, trivinylchlorosilane, m-allylphenylpropyl-dimethylchlorosilane, [2-(3-cyclohexenyl)ethyl]-dimethylchlorosilane, 5-norbornen-2-yl(ethyl)-dimethylchlorosilane, 3-isocyanatopropyldimethylchlorosilane, 3-methacryloxypropyldimethylchlorosilane, (3,3,3-trifluoropropyl)dimethylchlorosilane, 3,5-bis(trifluoromethyl)phenyldimethylchlorosilane, pentafluorophenyldimethylchlorosilane, pentafluorophenylpropyldimethylchlorosilane, 1H,1H,2H,2H-perfluorodecyldimethylchlorosilane, and 1H,1H,2H,2H-perfluorobctyldimethylchlorosilane.

When the functional group of the compound (1) is an addition-polymerizable or polycondensable group, then the compound (1) may be formed into a polymer. Any ordinary polymerization method is employable for it, including radical polymerization, anionic polymerization, cationic polymerization, metal-initiated polymerization, polycondensation, etc. The compound (1) may be copolymerized with any other monomer. In the resulting copolymer, the configuration of the constitutive units suggesting the compound (1) may be in any form of random, block or alternative copolymerization. The compound (1) may be grafted on any other polymer. Examples of the polymerizable group are alkenyl, —OH, carboxyl, 2-oxapropandioyl, oxiranyl, 3,4-epoxycyclohexyl, oxetanyl, oxetanylene and amino.

BEST MODE FOR CARRYING OUT THE INVENTION

The invention is described in more detail with reference to the following Examples, to which, however, the invention should not be limited. In the chemical formulae in the Examples, Ph is phenyl, Me is methyl, TMS is trimethylsilyl, Ac is acetyl. In the Examples, the mean molecular weight is determined as follows: The sample is analyzed through gel permeation chromatography (GPC) using THF as an eluent, and its calibration is drawn using standard polystyrene. From it, the mean molecular weight of the sample is calculated, and it is uncorrected. All nuclear magnetic resonance spectra are analyzed with JEOL GSX-400, using heavy chloroform as a solvent and tetramethylsilane as an internal standard substance. For the IR absorption spectrometry, used is JASCO FT/IR-7000.

EXAMPLE 1

<Production of Compound (3-1)>

Phenyltrimethoxysilane (6.54 kg), 2-propyl alcohol (26.3 liters), pure water (0.66 kg), and sodium hydroxide (0.88 kg) were put into a 50-liter reactor equipped with a reflux condenser, a thermometer and a stirrer, and sealed up with dry nitrogen. This is heated with stirring, and reacted for 5 hours under reflux. After the reaction, this was left at room temperature for 15 hours, and the supernatant was removed from the resulting reaction mixture through decantation. The resulting residue was led through a pressure filter device equipped with a membrane filter having a pore size of 0.1 μm, and a white solid was separated from it. The white solid was washed once with 2-propyl alcohol (9.87 kg). The substance was transferred into a stainless tray lined with a polytetrafluoroethylene sheet. Using a reduced-pressure drier, this was dried at an inner temperature of 80° C. and under a pressure of $6.7 \times 10^{-4}$ MPa for 24 hours, and 2.22 kg of a white powdery solid was thus obtained.

EXAMPLE 2

<Identification of Structure of Compound (3-1)>

The above-mentioned white powdery solid (1.2 g), THF (10 g) and triethylamine (1.6 g) were put into a 50-ml reactor equipped with a dropping funnel, a reflux condenser and a thermometer, and sealed up with dry nitrogen. The solution temperature was kept at 15° C. to 20° C. with stirring with a magnetic stirrer, and chlorotrimethylsilane (2.2 g) was dropwise added to it through the dropping funnel, taking about 1 minute. After the addition, this was continuously stirred at 15° C. for 3.5 hours. Next, deionized water (10 g) was added to it to dissolve the side product, sodium chloride, and the unreacted chlorotrimethylsilane was hydrolyzed. Thus obtained, the reaction mixture was separated into an organic layer and an aqueous layer through a liquid-liquid separation funnel. The resulting organic layer was washed with deionized water, and the washing was repeated until the pH of the wash waste could be neutral. Then, the organic layer was dried with anhydrous magnesium sulfate and concentrated under reduced pressure to obtain 1.2 g of a white solid.

The resulting white solid was analyzed through GPC, $^1$H-NMR and $^{29}$Si—NMR, and its structure was identified. The GPC chart thereof confirmed that the white solid is monodispersive and has a number-average molecular weight of 970 and a weight-average molecular weight of 990 in conversion to polystyrene. The $^1$H-NMR confirmed that phenyl group and trimethylsilyl group exist in an integral ratio of 8/4 in the product. The $^{29}$Si-NMR confirmed the existence of two signals suggesting a T-structure having phenyl, at −76.12 ppm and −78.95 ppm in an integral ratio of 1/1; and the existence of one signal suggesting a trimethylsilyl group at 10.62 ppm. The T structure is a structure of silicon atom bonding to three oxygen atoms. These analytic data support the structure of the following formula (a). Accordingly, it is judged that the compound before trimethylsilylation may have a chemical structure represented by Formula (3-1.

EXAMPLE 3

<Production of Silsesquioxane Derivative having Hydrosilyl Group>

The compound (3-1) obtained in Example 1 (69 g), and toluene (520 g) were put into a 1000-ml reactor equipped with a dropping funnel, a thermometer and a reflux condenser, and sealed up with dry nitrogen. While the solution temperature was kept at 23 to 38° C. with stirring with a magnetic stirrer, chlorodimethylsilane (80 g) was dropwise added to it through the dropping funnel, taking about 11 minutes. After the addition, this was heated in an oil bath with stirring, and reacted at 3 hours under reflux. After the reaction, this was cooled until the reaction solution could be 50° C. or lower. Next, unreacted chlorodimethylsilane was removed through single distillation, and then the reaction solution was concentrated until its amount could be about ½. This was cooled until the reaction solution could be 50° C. or lower, and then deionized water (150 g) was dropwise added to it through the dropping funnel. After the addition, this was stirred for 10 minutes, and then subjected to liquid-liquid separation into an organic layer and an aqueous layer. The organic layer was washed twice with 100 ml/one washing of deionized water. The resulting organic layer was dried with anhydrous magnesium sulfate, and then filtered, and concentrated under reduced pressure to obtain 71 g of a white solid. The white solid was extracted once with n-heptane (355 ml) to remove impurities, and then this was filtered and dried under reduced pressure to obtain 55 g of a white powdery solid.

Thus obtained, the white powdery solid was analyzed through IR spectrometry according to a KBr tablet method, and it confirmed an absorption based on the stretching motion of Si—H at 2142 cm$^{-1}$. The $^{29}$Si—NMR analysis of the product confirmed a signal of dimethylsilyl group at −3.81 ppm. The $^1$H-NMR analysis confirmed the integral ratio based on Ph group, SiH group and Me group of 40/4/24. The GPC analysis confirmed the number-average molecular weight of the product of 930 and the weight-average molecular weight thereof of 980. These data suggest that the white powdery solid is a compound having a chemical structure represented by Formula (7).

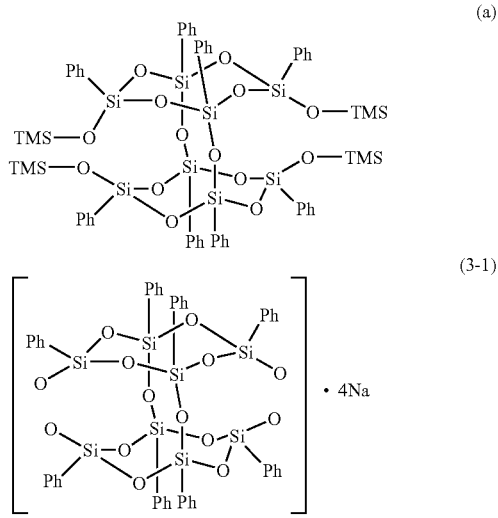

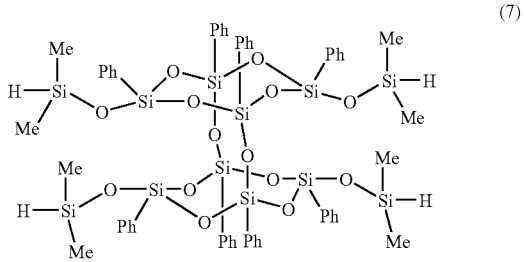

EXAMPLE 4

<Production of Silsesquioxane Derivative having Glycidyl Group>

The compound (7) obtained in Example 3 (2.0 g), allyl glycidyl ether (1.4 g) and toluene (3.4 g) were put into a 50-ml reactor equipped with a thermometer, a dropping funnel and a reflux condenser, and sealed up with dry nitrogen. With stirring with a magnetic stirrer, the reaction solution was heated up to 70° C. Karstedt catalyst (2.0 μl) was added to it through a microsyringe, and then this was kept stirred for 1 hour. Then, the reaction solution was sampled and subjected to IR analysis. This confirmed the disappearance of the absorption suggesting Si—H group at 2138 cm$^{-1}$. Next, the reaction solution was concentrated under reduced pressure to obtain 2.5 g of a viscous liquid.

The resulting viscous liquid was subjected to $^{29}$Si-NMR analysis. This confirmed a signal at 11.42 ppm corresponding to a glycidoxypropyldimethylsilyl group. The GPC analysis confirmed the number-average molecular weight of the product of 1100 and the weight-average molecular weight thereof of 1170. These data suggest that the viscous liquid is a compound having a chemical structure represented by Formula disappearance of the absorption suggesting Si—H group at 2138 cm$^{-1}$. Next, the reaction solution was concentrated under reduced pressure, and the resulting residue was diluted with ethyl acetate (28 g) to a 20 wt. % dilution. Next, powdery active charcoal (0.4 g) was added to it, and kept stirred for 1.5 hours. Then, the active charcoal was removed through filtration, and the filtrate was concentrated under reduced pressure to obtain 6.6 g of a viscous liquid.

The resulting viscous liquid was subjected to IR analysis according to a liquid-membrane process. This confirmed an absorption owing to the O—H stretching vibration of the hydroxyl group at 3450 cm$^{-1}$. The $^{29}$Si—NMR analysis of

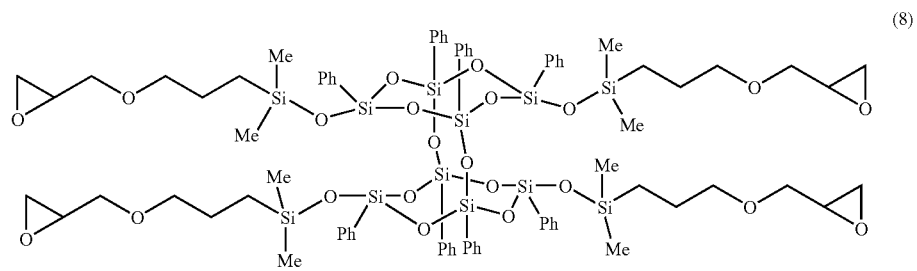

(8)

EXAMPLE 5

<Production of Silsesquioxane Derivative having Hydroxyl Group>

The compound (7) (5.2 g), 2-allyloxyethanol (6.6 g) and toluene (5.2 g) were put into the same reactor as that used the product confirmed a peak corresponding to a (3-(2-hydroxyethyloxy)propyl)dimethylsilyl group at 11.42 ppm. The GPC analysis confirmed the number-average molecular weight of the product of 1180 and the weight-average molecular weight thereof of 1230. These data suggest that the viscous liquid is a compound having a chemical structure represented by Formula (9).

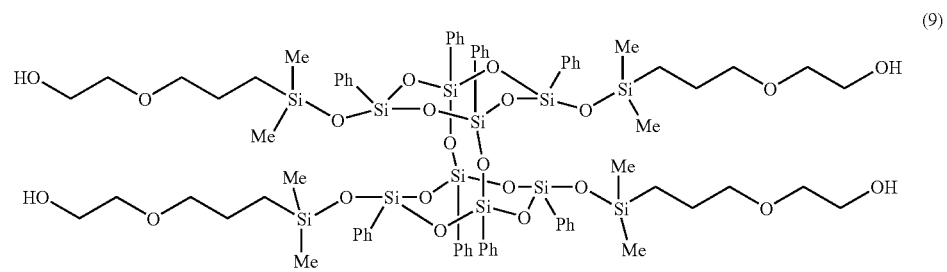

(9)

in Example 4, and sealed up with dry nitrogen. With stirring with a magnetic stirrer, the reaction solution was heated up to 42° C. Karstedt catalyst (33 μl) was added to it through a microsyringe, and then this was kept stirred for 2 hours while heated at 60° C. Then, the reaction solution was sampled and subjected to IR analysis. This confirmed the

EXAMPLE 6

<Production of Silsesquioxane Derivative having Acetoxy Group>

The compound (7) (10.4 g), 2-allyloxyethyl ester acetate (6.9 g) prepared from 2-allyloxyethanol and acetyl chloride, and toluene (17.3 g) were put into the same reactor as that used in Example 4, and sealed up with dry nitrogen. With stirring with a magnetic stirrer, the reaction solution was heated up to 56° C. Karstedt catalyst (10 μl) was added to it through a microsyringe, and then this was kept stirred for 4 hours while heated at 80° C. Then, the reaction solution was sampled and subjected to IR analysis. This confirmed the disappearance of the absorption suggesting Si—H at 2138 cm$^{-1}$. Next, the reaction solution was concentrated under reduced pressure to obtain 15.3 g of a viscous liquid.

The resulting viscous liquid was subjected to IR analysis according to a liquid-membrane process. This confirmed an absorption owing to the C=O stretching vibration at 1739 cm$^{-1}$. The $^{29}$Si-NMR analysis of the product confirmed a signal corresponding to a (3-(2-acetoxyethoxy)propyl)dimethylsilyl group at 11.41 ppm. The $^{13}$C-NMR analysis of the product confirmed a signal derived from the C=O group at 170.83 ppm. The GPC analysis confirmed the number-average molecular weight of the product of 1460 and the weight-average molecular weight thereof of 1510. These data suggest that the viscous liquid is a compound having a chemical structure represented by Formula (10).

that used in Example 4, and sealed up with dry nitrogen. With stirring with a magnetic stirrer, the reaction solution was heated up to 80° C. Karstedt catalyst (4.0 μl) was added to it through a microsyringe, and then this was kept stirred for 1 hour. Then, the reaction solution was sampled and subjected to IR analysis. This confirmed the disappearance of the absorption suggesting Si—H group at 2138 cm$^{-1}$. Next, the reaction solution was concentrated under reduced pressure to obtain 7.7 g of a viscous liquid. Methyl alcohol (6.1 g) was added to the resulting viscous liquid, and this was kept stirred for 4 hours with a magnetic stirrer at 27° C. Next, powdery active charcoal (0.23 g) was added to the solution and kept stirred for 1 hour. The active charcoal was removed through filtration, and the filtrate was concentrated under reduced pressure to obtain 6.2 g of a white solid.

The resulting white solid was subjected to $^{13}$C-NMR analysis. This confirmed a peak suggesting a carboxyl group

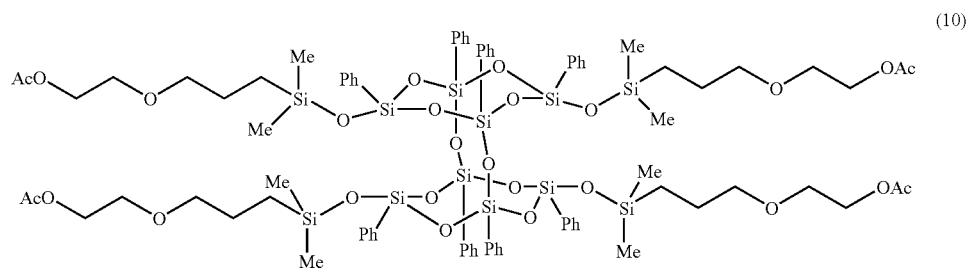

(10)

EXAMPLE 7

<Production of Silsesquioxane Derivative having Carboxyl Group>

The compound (7) (5.2 g), trimethylsilyl 4-pentenoate (3.0 g), and toluene (7.5 g) were put into the same reactor as at 180.44 ppm. The GPC analysis confirmed the number-average molecular weight of the product of 1490 and the weight-average molecular weight thereof of 1550. These data suggest that the white solid is a compound having a chemical structure represented by Formula (11).

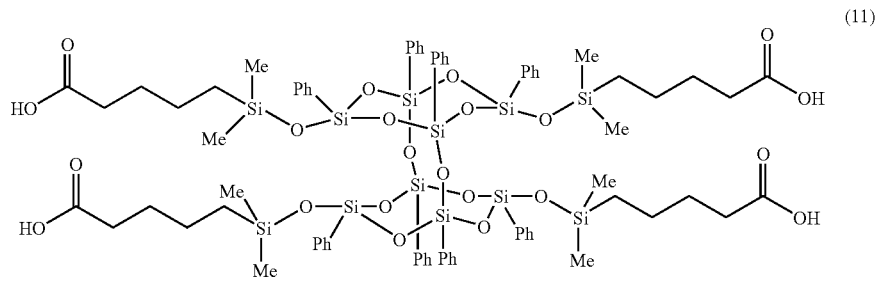

(11)

EXAMPLE 8

<Production of Silsesquioxane Derivative having Methacryloxy Group>

The compound (3-1) produced in Example 1 (1.2 g), THF (20 g) and triethylamine (8.1 g) were put into the same reactor as that used in Example 4, and sealed up with dry nitrogen. While the reaction solution was kept at 5 to 10° C. with stirring with a magnetic stirrer, methacryloxypropyldimethylchlorosilane (18 g) was dropwise added to it through the dropping funnel, taking about 11 minutes, and then this was kept stirred for 5 hours. After the reaction, deionized water (10 g) was dropwise added to it via the dropping funnel, and this was separated into an organic layer and an aqueous layer through a liquid-liquid separation funnel. The organic layer was repeatedly washed with deionized water and it became neutral. Thus obtained, the organic layer was dried with anhydrous magnesium sulfate, and then concentrated under reduced pressure to obtain 15 g of a viscous liquid. The viscous liquid was purified through silica gel column chromatography, using a mixed solvent of n-hexane/acetate ethyl (5/1 by volume), and 1.5 g of a white solid was obtained.

The resulting white solid was analyzed through IR spectrometry according to a KBr tablet method, and it confirmed an absorption based on the stretching motion of C=O at 1718 cm$^{-1}$. The $^{29}$Si—NMR analysis of the product confirmed a peak suggesting a 3-methacryloxypropyldimethylsilyl group at 11.02 ppm. The GPC analysis confirmed the number-average molecular weight of the product of 1180 and the weight-average molecular weight thereof of 1210. These data suggest that the white solid is a compound having a chemical structure represented by Formula (12).

funnel, taking about 3 minutes, and then this was kept stirred for 4 hours. Next, deionized water (30 g) was gradually and dropwise added to it. After the reaction, this was separated into an organic layer and an aqueous layer through a liquid-liquid separation funnel. The organic layer was washed once with an aqueous solution of 0.1 N hydrochloric acid, and then three times with deionized water. Thus obtained, the organic layer was dried with anhydrous magnesium sulfate, and then concentrated under reduced pressure to obtain 8.0 g of a viscous liquid. The viscous liquid was recrystallized from methyl alcohol (120 g), and 4.2 g of a white solid was obtained.

The resulting white solid was analyzed through IR spectrometry according to a KBr tablet method, and it confirmed an absorption based on the stretching motion of C—Cl group at 787 cm$^{-1}$. The $^1$H-NMR analysis of the product confirmed a triplet-divided signal derived from —CH$_2$Cl group at 3.0 ppm. The $^{13}$C-NMR analysis of the product confirmed a signal derived from —CH$_2$Cl group at 47.36 ppm. The $^{29}$Si-NMR analysis of the product confirmed a signal for a 3-chloropropyldimethylsilyl group at 10.84 ppm. The GPC analysis confirmed the number-average molecular weight of the product of 1130 and the weight-average molecular weight thereof of 1140. These data suggest that the white solid is a compound having a chemical structure represented by Formula (13).

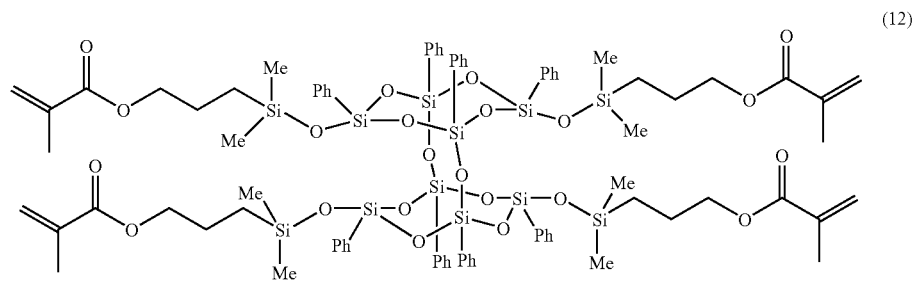

(12)

EXAMPLE 9

<Production of Silsesquioxane Derivative having 3-Chloropropyl Group>

The compound (3-1) (5.8 g), THF (50 g) and triethylamine (5.0 g) were put into the same reactor as that used in Example 4, and sealed up with dry nitrogen. While the reaction solution was kept at 28 to 41° C. with stirring with a magnetic stirrer, 3-chloropropyldimethylchlorosilane (10.3 g) was dropwise added to it through the dropping

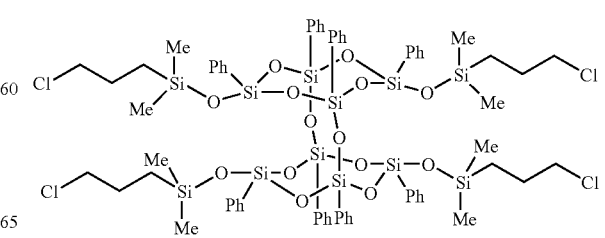

(13)

INDUSTRIAL APPLICABILITY

The invention provides a novel silsesquioxane derivative represented by Formula (1), and a method for producing it within a short period of time at a high yield. The silsesquioxane derivative of the invention is expected to have an improved compatibility with general organic polymers, and when it has a functional group, then the derivative is extremely useful as a reactivity modifier for general organic polymers.

The invention claimed is:

1. A silsesquioxane derivative represented by Formula (1):

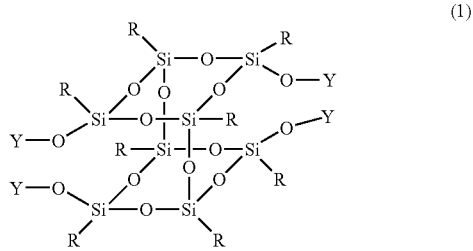

wherein each R is a group independently selected from hydrogen, alkyl having 1 to 45 carbon atoms in which any hydrogen may be replaced by fluorine and any —$CH_2$— may be replaced by —O—, —CH=CH—, cycloalkylene or cycloalkenylene, substituted or unsubstituted aryl, and arylalkyl composed of a substituted or unsubstituted aryl group and an alkylene group in which any hydrogen may be replaced by fluorine and any —$CH_2$— may be replaced by —O—, —CH=CH— or cycloalkylene; at least one Y is a group selected from the group represented by Formula (2), and the other Y is hydrogen; when at least two Y's are a group represented by Formula (2), then they may be the same group or may be composed of at least two different groups;

wherein $R^1$ and $R^2$ are independently a group defined similarly to R; and Z is a group defined similarly to R, or a functional group, or a group having a functional group.

2. The silsesquioxane derivative according to claim 1, wherein each R is a group independently selected from hydrogen, alkyl having 1 to 45 carbon atoms in which any hydrogen may be replaced by fluorine and any —$CH_2$— may be replaced by —O—, —CH=CH—, cycloalkylene or cycloalkenylene, substituted or unsubstituted aryl, and arylalkyl composed of a substituted or unsubstituted aryl group and an alkylene group in which any hydrogen may be replaced by fluorine and any —$CH_2$— may be replaced by —O—, —CH=CH— or cycloalkylene; $R^1$ and $R^2$ are independently methyl, isopropyl, tert-butyl or phenyl; and Z is a group defined similarly to R, or a functional group, or a group having a functional group.

3. The silsesquioxane derivative according to claim 2, wherein each R is a group independently selected from hydrogen, and alkyl having 1 to 30 carbon atoms in which any hydrogen may be replaced by fluorine and any —$CH_2$— may be replaced by —O— or cycloalkylene.

4. The silsesquioxane derivative according to claim 2, wherein each R is a group independently selected from alkenyl having 2 to 20 carbon atoms in which any hydrogen may be replaced by fluorine and any —$CH_2$— may be replaced by —O— or cycloalkylene, and alkyl having 1 to 20 carbon atoms in which any hydrogen may be replaced by fluorine and at least one —$CH_2$— is replaced by cycloalkenylene.

5. The silsesquioxane derivative according to claim 2, wherein each R is a group independently selected from phenyl in which any hydrogen may be replaced by halogen or alkyl having 1 to 10 carbon atoms, and naphthyl; in the alkyl as the substituent for the phenyl, any hydrogen may be replaced by fluorine and any —$CH_2$— may be replaced by —O—, —CH=CH—, cycloalkylene or phenylene; and when the phenyl has plural substituents, the substituents may be the same group or different groups.

6. The silsesquioxane derivative according to claim 2, wherein each R is a group independently selected from phenylalkyl composed of a phenyl group in which any hydrogen may be replaced by halogen or alkyl having 1 to 10 carbon atoms and an alkylene group having 1 to 12 carbon atoms; in the alkyl as the substituent for the phenyl group, any hydrogen may be replaced by fluorine and any —$CH_2$— may be replaced by —O—, —CH=CH—, cycloalkylene or phenylene; in the alkylene group, any hydrogen may be replaced by fluorine and any —$CH_2$— may be replaced by —O— or cycloalkylene; and when the phenyl group has plural substituents, the substituents may be the same group or different groups.

7. The silsesquioxane derivative according to claim 2, wherein each R is a group independently selected from phenylalkenyl composed of a phenyl group in which any hydrogen may be replaced by halogen or alkyl having 1 to 10 carbon atoms and an alkenylene group having 2 to 12 carbon atoms; in the alkyl as the substituent for the phenyl group, any hydrogen may be replaced by fluorine and any —$CH_2$— may be replaced by —O—, —CH=CH—, cycloalkylene or phenylene; in the alkenylene group, any hydrogen may be replaced by fluorine and any —$CH_2$— may be replaced by —O— or cycloalkylene; and when the phenyl group has plural substituents, the substituents may be the same group or different groups.

8. The silsesquioxane derivative according to claim 2, wherein each R is a group independently selected from alkyl having 1 to 8 carbon atoms in which any hydrogen may be replaced by fluorine and any —$CH_2$— may be replaced by —O—, —CH=CH—, cycloalkylene or cycloalkenylene, phenyl in which any hydrogen may be replaced by halogen, methyl or methoxy, phenylalkyl composed of a phenyl group in which any hydrogen may be replaced by fluorine, alkyl having 1 to 4 carbon atoms, vinyl or methoxy, and an alkylene group having 1 to 8 carbon atoms in which any —$CH_2$— may be replaced by —O—, —CH=CH— or cycloalkylene, and naphthyl; when the phenyl group of the phenyl or the phenylalkyl has plural substituents, the substituents may be the same group or different groups.

9. The silsesquioxane derivative according to claim 2, wherein all R's are the same group selected from alkyl having 1 to 8 carbon atoms in which any hydrogen may be replaced by fluorine and any —$CH_2$— may be replaced by —O—, —CH=CH—, cycloalkylene or cycloalkenylene, phenyl in which any hydrogen may be replaced by halogen, methyl or methoxy, phenylalkyl composed of a phenyl group in which any hydrogen may be replaced by fluorine, alkyl having 1 to 4 carbon atoms, vinyl or methoxy, and an alkylene group having 1 to 8 carbon atoms in which any —$CH_2$— may be replaced by —O—, —CH=CH— or cycloalkylene, and naphthyl; when the phenyl group of the phenyl or the phenylalkyl has plural substituents, the substituents may be the same group or different groups.

10. The silsesquioxane derivative according to claim 2, wherein all R's are the same group selected from phenyl in which any hydrogen may be replaced by halogen, methyl or methoxy, phenylalkyl composed of a phenyl group in which any hydrogen may be replaced by fluorine, alkyl having 1 to 4 carbon atoms, vinyl or methoxy, and an alkylene group having 1 to 8 carbon atoms in which any —$CH_2$— may be replaced by —O—, —CH=CH— or cycloalkylene, and naphthyl; when the phenyl group of the phenyl or the phenylalkyl has plural substituents, the substituents may be the same group or different groups.

11. The silsesquioxane derivative according to claim 2, wherein all R's are phenyl.

12. A silsesquioxane derivative represented by Formula (1):

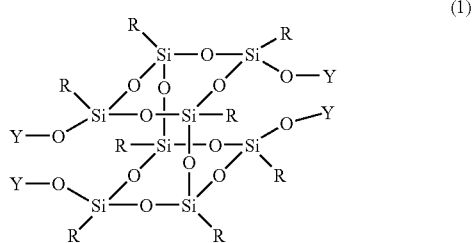

wherein each R is a group independently selected from hydrogen, alkyl having 1 to 45 carbon atoms in which any hydrogen may be replaced by fluorine and any —$CH_2$— may be replaced by —O—, —CH=CH—, cycloalkylene or cycloalkenylene, substituted or unsubstituted aryl, and arylalkyl composed of a substituted or unsubstituted aryl group and an alkylene group in which any hydrogen may be replaced by fluorine and any —$CH_2$— may be replaced by —O—, —CH=CH— or cycloalkylene; at least one Y is a group selected from the group represented by Formula (2), and the other Y is hydrogen; when at least two Y's are a group represented by Formula (2), then they may be the same group or may be composed of at least two different groups;

wherein $R^1$ and $R^2$ are independently methyl, isopropyl, tert-butyl or phenyl; and Z is a functional group selected from hydrogen (bonding to Si), halogen, —OH, fluoroalkyl, alkoxy, carboxyl, 2-oxapropanedioyl, —COO—, —OCO—, polyalkyleneoxy, oxiranyl, 3,4-epoxycyclohexyl, oxetanyl, oxetanylene, alkenyl, cycloalkenyl, —$NH_2$, —NH—, —CN, —NCO, —SH and —$PH_2$, or a group having the functional group.

13. The silsesquioxane derivative according to claim 12, wherein each R is a group independently selected from hydrogen, and alkyl having 1 to 30 carbon atoms in which any hydrogen may be replaced by fluorine and any —$CH_2$— may be replaced by —O— or cycloalkylene.

14. The silsesquioxane derivative according to claim 12, wherein each R is a group independently selected from alkenyl having 2 to 20 carbon atoms in which any hydrogen may be replaced by fluorine and any —$CH_2$— may be replaced by —O— or cycloalkylene, and alkyl having 1 to 20 carbon atoms in which any hydrogen may be replaced by fluorine and at least one —$CH_2$— is replaced by cycloalkenylene.

15. The silsesquioxane derivative according to claim 12, wherein each R is a group independently selected from phenyl in which any hydrogen may be replaced by halogen or alkyl having 1 to 10 carbon atoms, and naphthyl; in the alkyl as the substituent for the phenyl, any hydrogen may be replaced by fluorine and any —$CH_2$— may be replaced by —O—, —CH=CH—, cycloalkylene or phenylene; and when the phenyl has plural substituents, the substituents may be the same group or different groups.

16. The silsesquioxane derivative according to claim 12, wherein each R is a group independently selected from phenylalkyl composed of a phenyl group in which any hydrogen may be replaced by halogen or alkyl having 1 to 10 carbon atoms and an alkylene group having 1 to 12 carbon atoms; in the alkyl as the substituent for the phenyl group, any hydrogen may be replaced by fluorine and any —$CH_2$— may be replaced by —O—, —CH=CH—, cycloalkylene or phenylene; in the alkylene group, any hydrogen may be replaced by fluorine and any —$CH_2$— may be replaced by —O— or cycloalkylene; and when the phenyl group has plural substituents, the substituents may be the same group or different groups.

17. The silsesquioxane derivative according to claim 12, wherein each R is a group independently selected from phenylalkenyl composed of a phenyl group in which any hydrogen may be replaced by halogen or alkyl having 1 to 10 carbon atoms and an alkenylene group having 2 to 12 carbon atoms; in the alkyl as the substituent for the phenyl group, any hydrogen may be replaced by fluorine and any —$CH_2$— may be replaced by —O—, —CH=CH—, cycloalkylene or phenylene; in the alkenylene group, any hydrogen may be replaced by fluorine and any —$CH_2$— may be replaced by —O— or cycloalkylene; and when the phenyl group has plural substituents, the substituents may be the same group or different groups.

18. The silsesquioxane derivative according to claim 12, wherein each R is a group independently selected from alkyl having 1 to 8 carbon atoms in which any hydrogen may be replaced by fluorine and any —$CH_2$— may be replaced by —O—, —CH=CH—, cycloalkylene or cycloalkenylene, phenyl in which any hydrogen may be replaced by halogen, methyl or methoxy, phenylalkyl composed of a phenyl group in which any hydrogen may be replaced by fluorine, alkyl having 1 to 4 carbon atoms, vinyl or methoxy, and an alkylene group having 1 to 8 carbon atoms in which any —$CH_2$— may be replaced by —O—, —CH=CH— or cycloalkylene, and naphthyl; when the phenyl group of the phenyl or the phenylalkyl has plural substituents, the substituents may be the same group or different groups.

19. The silsesquioxane derivative according to claim 12, wherein all R's are the same group selected from alkyl having 1 to 8 carbon atoms in which any hydrogen may be replaced by fluorine and any —$CH_2$— may be replaced by —O—, —CH=CH—, cycloalkylene or cycloalkenylene, phenyl in which any hydrogen may be replaced by halogen, methyl or methoxy, phenylalkyl composed of a phenyl group in which any hydrogen may be replaced by fluorine, alkyl having 1 to 4 carbon atoms, vinyl or methoxy, and an alkylene group having 1 to 8 carbon atoms in which any —CH$_2$— may be replaced by —O—, —CH=CH— or cycloalkylene, and naphthyl; when the phenyl group of the phenyl or the phenylalkyl has plural substituents, the substituents may be the same group or different groups.

20. The silsesquioxane derivative according to claim 12, wherein all R's are the same group selected from phenyl in which any hydrogen may be replaced by halogen, methyl or methoxy, phenylalkyl composed of a phenyl group in which any hydrogen may be replaced by fluorine, alkyl having 1 to 4 carbon atoms, vinyl or methoxy, and an alkylene group having 1 to 8 carbon atoms in which any —CH$_2$— may be replaced by —O—, —CH=CH— or cycloalkylene, and naphthyl; when the phenyl group of the phenyl or the phenylalkyl has plural substituents, the substituents may be the same group or different groups.

21. The silsesquioxane derivative according to claim 12, wherein all R's are phenyl.

22. The silsesquioxane derivative according to claim 12, wherein Z is halogenated alkyl or a group having halogenated alkyl.

23. The silsesquioxane derivative according to claim 12, wherein Z is alkenyl, or a group having any of alkenyl, —OH, carboxyl, 2-oxapropanedioyl, oxiranyl, 3,4-epoxycyclohexyl, oxetanyl, oxetanylene and —NH$_2$.

24. A method for producing the silsesquioxane derivative defined in claim 12, which comprises reacting a silsesquioxane derivative represented by Formula (3) with a compound represented by Formula (4) to give a compound represented by Formula (5), and hydrosilylating it with a compound having a functional group Z and an unsaturated hydrocarbon group:

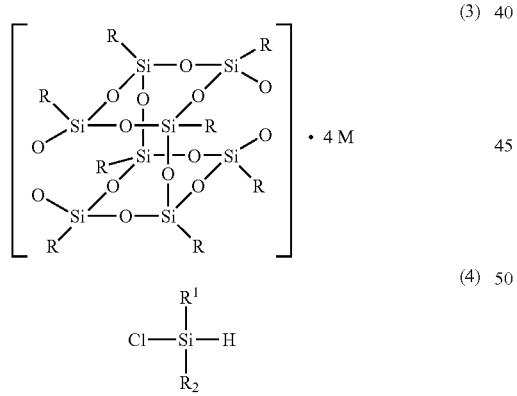

(3)

(4)

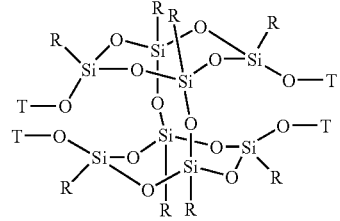

(5)

wherein R has the same meaning as that of R in Formula (1); M is a monovalent alkali metal atom; R$^1$ and R$^2$ have the same meanings as those in Formula (2); at least one T is the following group that is derived from Formula (4) by removing Cl, and the other T is hydrogen.

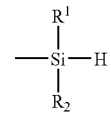

25. A method for producing the silsesquioxane derivative defined in claim 12, which comprises reacting a silsesquioxane derivative represented by Formula (3) with a compound represented by Formula (6):

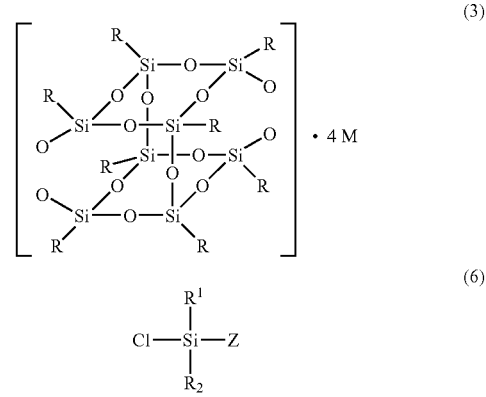

(3)

(6)

wherein R has the same meaning as that of R in Formula (1); M is a monovalent alkali metal atom; R$^1$, R$^2$ and Z have the same meanings as those in Formula (2).

26. A polymer obtained by addition-polymerization or polycondensation of the silsesquioxane derivative defined in claim 23.

* * * * *